(12) United States Patent
Marinkovic et al.

(10) Patent No.: US 10,314,819 B2
(45) Date of Patent: Jun. 11, 2019

(54) SOLID STATE FORMS OF ELUXADOLINE

(71) Applicant: TEVA PHARMACEUTICALS INTERNATIONAL GMBH, Jona (CH)

(72) Inventors: Marina Marinkovic, Zagreb (HR); Vitomir Vusak, Zagreb (HR); Edislav Leksic, Zagreb (HR); Sanja Matecic Musanic, Zagreb (HR)

(73) Assignee: TEVA PHARMACEUTICALS INTERNATIONAL GMBH, Jona (CH)

( * ) Notice: Subject to any disclaimer, the term of this patent is extended or adjusted under 35 U.S.C. 154(b) by 0 days.

(21) Appl. No.: 15/745,228

(22) PCT Filed: Jul. 22, 2016

(86) PCT No.: PCT/US2016/043678
§ 371 (c)(1),
(2) Date: Jan. 16, 2018

(87) PCT Pub. No.: WO2017/015606
PCT Pub. Date: Jan. 26, 2017

(65) Prior Publication Data
US 2018/0228773 A1 Aug. 16, 2018

Related U.S. Application Data

(60) Provisional application No. 62/260,972, filed on Nov. 30, 2015, provisional application No. 62/254,517, filed on Nov. 12, 2015, provisional application No. 62/250,128, filed on Nov. 3, 2015, provisional application No. 62/195,959, filed on Jul. 23, 2015.

(51) Int. Cl.
*A61P 1/12* (2006.01)
*C07D 233/64* (2006.01)
*A61K 31/4164* (2006.01)

(52) U.S. Cl.
CPC .......... *A61K 31/4164* (2013.01); *A61P 1/12* (2018.01); *C07D 233/64* (2013.01)

(58) Field of Classification Search
CPC ..... A61K 31/4164; A61P 1/12; C07D 233/64; B62D 25/105; B62D 25/12; B62D 35/00; B62D 35/005; B62D 37/02
See application file for complete search history.

(56) References Cited

U.S. PATENT DOCUMENTS

| | | |
|---|---|---|
| 7,741,356 B2 | 6/2010 | Breslin et al. |
| 7,994,206 B2 | 8/2011 | Anzalone et al. |
| 8,609,865 B2 | 12/2013 | Anzalone et al. |
| 8,691,860 B2 | 4/2014 | Anzalone et al. |
| 8,859,604 B2 | 10/2014 | Anzalone et al. |
| 9,115,091 B2 | 8/2015 | Anzalone et al. |
| 9,364,489 B2 | 6/2016 | Anzalone et al. |
| 9,789,125 B2 | 10/2017 | Anzalone et al. |

FOREIGN PATENT DOCUMENTS

| | | |
|---|---|---|
| WO | 2009009480 A2 | 1/2009 |
| WO | 2017114446 A1 | 7/2017 |
| WO | 2017153471 A1 | 9/2017 |
| WO | 2017191650 A1 | 11/2017 |
| WO | 2018020450 A2 | 2/2018 |
| WO | 2018047131 A1 | 3/2018 |
| WO | 2018138272 A1 | 8/2018 |
| WO | 2018138274 A1 | 8/2018 |
| WO | 2018185664 A1 | 10/2018 |
| WO | 2018185711 A1 | 10/2018 |
| WO | 2018198101 A2 | 11/2018 |

OTHER PUBLICATIONS

International Search Report for International Application No. PCT/US2016/043678, International Filing Date Jul. 22, 2016, dated Nov. 8, 2016, 6 pages.

Written Opinion for International Application No. PCT/US2016/043678, International Filing Date Jul. 11, 2016, dated Nov. 8, 2016, 9 pages.

*Primary Examiner* — Umamaheswari Ramachandran
(74) *Attorney, Agent, or Firm* — Cantor Colburn LLP

(57) ABSTRACT

Disclosed are solid state forms of Eluxadoline, processes for their preparations, compositions comprising them and their medical use. The present invention also encompasses solid state forms of Eluxadoline for use in the preparation of other solid state forms of Eluxadoline, particularly form alpha.

17 Claims, 22 Drawing Sheets

SEM image of stable Amorphous Eluxadoline prepared according to Example 20

SEM image of stable Amorphous Eluxadoline prepared according to Example 21

SEM images of stable Eluxadoline form alpha of Example 19

(2000x magnification):

(5000x magnification):

SEM image of stable Eluxadoline form alpha prepared according to Example 22

SOLID STATE FORMS OF ELUXADOLINE

CROSS-REFERENCE TO RELATED APPLICATIONS

This application is a National Stage application of PCT/US2016/043678, filed 22 Jul. 2016, and is related to, and claims the benefit of priority of, U.S. Provisional Application No. 62/195,959 filed on 23 Jul. 2015, U.S. Provisional Application No. 62/250,128 filed on 3 Nov. 2015, U.S. Provisional Application No. 62/254,517 filed on 12 Nov. 2015, and U.S. Provisional Application No. 62/260,972 filed on 30 Nov. 2015, all of which are entitled SOLID STATE FORMS OF ELUXADOLINE, the contents of which are incorporated herein by reference in their entirety for all purposes.

FIELD OF THE INVENTION

The present invention encompasses solid state forms of Eluxadoline, processes for their preparations, compositions comprising them and their medical use. The present invention also encompasses solid state forms of Eluxadoline for use in the preparation of other solid state forms of Eluxadoline, particularly form alpha.

BACKGROUND OF THE INVENTION

Eluxadoline, 5-[[[(2S)-2-amino-3-(4-carbamoyl-2,6-dimethylphenyl)propanoyl]-[(1S)-1-(5-phenyl-1H-imidazol-2-yl)ethyl]amino]methyl]-2-methoxybenzoic acid, has the following formula:

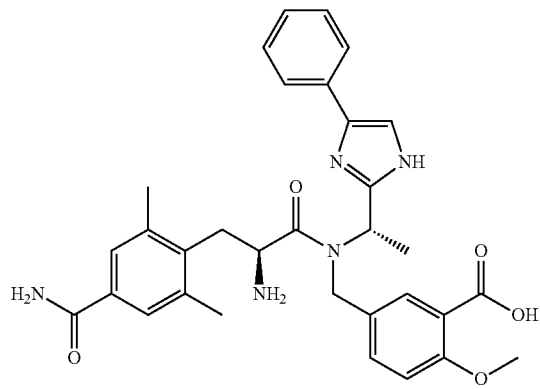 [SMILES: COc1ccc(CN(C(=O)[C@@H](N)Cc2c(C)cc(C(N)=O)cc2C)[C@@H](C)c2nc(-c3ccccc3)c[nH]2)cc1C(=O)O]

Eluxadoline is developed for the treatment of irritable bowel syndrome with diarrhea (IBS-D).

U.S. Pat. No. 7,741,356 discloses Eluxadoline and its activity as opioid receptor modulator.

U.S. Pat. Nos. 7,994,206, 8,609,865, 8,691,860 and 859,604 describe two crystalline forms, alpha and beta, of Eluxadoline. It also discloses a process for preparing a crystalline zwitterion.

Polymorphism, the occurrence of different crystalline forms, is a property of some molecules and molecular complexes. A single molecule may give rise to a variety of polymorphs having distinct crystal structures and physical properties like melting point, thermal behaviors (e.g. measured by thermogravimetric analysis—"TGA", or differential scanning calorimetry—"DSC"), X-ray diffraction pattern, infrared absorption fingerprint, and solid state ($^{13}$C—) NMR spectrum. One or more of these techniques may be used to distinguish different polymorphic forms of a compound.

Different salts and solid state forms (including solvated forms) of an active pharmaceutical ingredient may possess different properties. Such variations in the properties of different salts and solid state forms and solvates may provide a basis for improving formulation, for example, by facilitating better processing or handling characteristics, changing the dissolution profile in a favorable direction, or improving stability (polymorph as well as chemical stability) and shelf-life. These variations in the properties of different salts and solid state forms may also offer improvements to the final dosage form, for instance, if they serve to improve bioavailability. Different salts and solid state forms and solvates of an active pharmaceutical ingredient may also give rise to a variety of polymorphs or crystalline forms, which may in turn provide additional opportunities to assess variations in the properties and characteristics of a solid active pharmaceutical ingredient.

Discovering new salts, solid state forms and solvates of a pharmaceutical product may yield materials having desirable processing properties, such as ease of handling, ease of processing, storage stability, and ease of purification or as desirable intermediate crystal forms that facilitate conversion to other polymorphic forms. New solid state forms of a pharmaceutically useful compound can also provide an opportunity to improve the performance characteristics of a pharmaceutical product. It enlarges the repertoire of materials that a formulation scientist has available for formulation optimization, for example by providing a product with different properties, e.g., a different crystal habit, higher crystallinity or polymorphic stability which may offer better processing or handling characteristics, improved dissolution profile, or improved shelf-life (chemical/physical stability). For at least these reasons, there is a need for additional salts and solid state forms (including solvated forms) of Eluxadoline.

SUMMARY OF THE INVENTION

The present invention provides solid state forms of Eluxadoline and pharmaceutical compositions thereof.

The present invention provides solid state forms of Eluxadoline for use in the preparation of pharmaceutical compositions and/or formulations of this compound.

The present invention also encompasses the use of the solid state forms of Eluxadoline of the present invention for the preparation of pharmaceutical compositions and/or formulations of this compound.

The present invention comprises a process for preparing the above mentioned pharmaceutical formulations. The process comprises combining the Eluxadoline with at least one pharmaceutically acceptable excipient.

The Eluxadoline solid state forms, and the pharmaceutical compositions and/or formulations of the present invention can be used as medicaments, particularly for the treatment of irritable bowel syndrome with diarrhea (IBS-D).

The present invention further provides solid state forms of Eluxadoline for use in the preparation of other solid state forms of Eluxadoline, or other salts of Eluxadoline and their solid state forms, in particular Eluxadoline form alpha, form I, form II, form III and form IV.

DETAILED DESCRIPTION OF THE INVENTION

Figure 1:
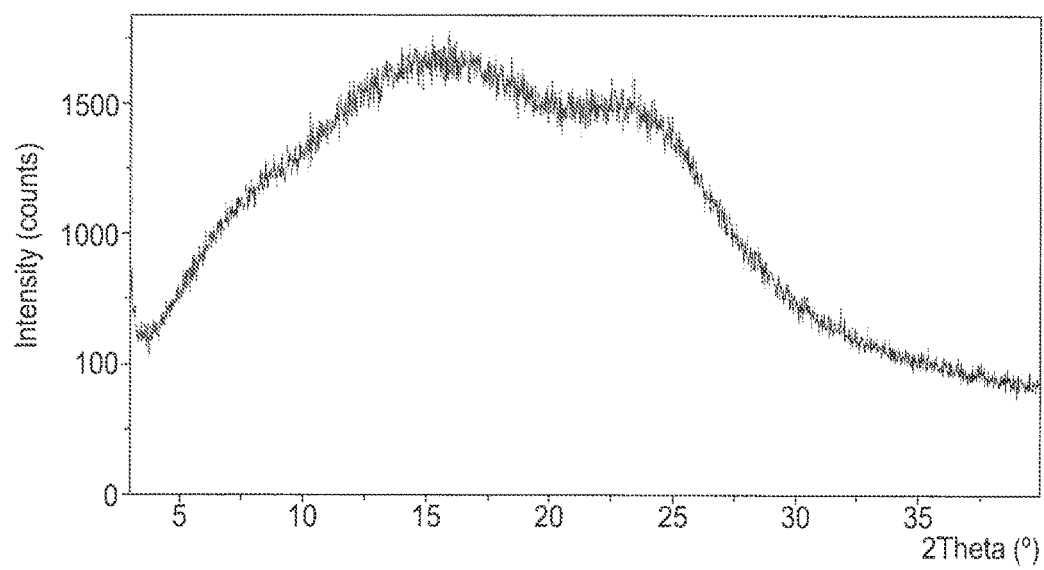
FIG. 1 shows an X-ray powder diffractogram ("PXRD" or "XRPD") of Eluxadoline amorphous form.

The present invention encompasses solid state forms of Eluxadoline, processes for their preparations, compositions comprising them and their medical use. The present invention also encompasses solid state forms of Eluxadoline for use in the preparation of other solid state forms of Eluxadoline, particularly form alpha.

Solid state properties of Eluxadoline can be influenced by controlling the conditions under which the Eluxadoline is obtained in solid form.

In some embodiments, the solid state forms of Eluxadoline of the invention are substantially free of any other forms of Eluxadoline. As used herein in this context, the expression "substantially free of any other forms" will be understood to mean that the solid state form contains 20% or less, 10% or less, 5% or less, 2% or less, or 1% or less of any other forms of the subject compound as measured, for example, by XRPD. Thus, a solid state of Eluxadoline described herein as substantially free of any other solid state forms would be understood to contain greater than 80% (w/w), greater than 90% (w/w), greater than 95% (w/w), greater than 98% (w/w), or greater than 99% (w/w) of the subject solid state form of Eluxadoline. Accordingly, in some embodiments of the invention, the described solid state forms of Eluxadoline may contain from 1% to 20% (w/w), from 5% to 20% (w/w), or from 5% to 10% (w/w) of one or more other solid state forms of Eluxadoline.

As used herein, the term chemically pure refers to a material which is substantially free of chemical impurities, such as reaction by-products, un-reacted intermediates or degradation product. The term "substantially free" is meant that the chemically pure material of the present invention contains 3% (w/w) or less of chemical impurities. According to some embodiments, the chemically pure material of the present invention contains 3% (w/w) or less, 2% (w/w) or less, 1% (w/w) or less, 0.5% (w/w) or less, or 0.2% (w/w) or less of chemical impurities. In other embodiments, a chemically pure material of the present invention contains from 0.01% to 3% (w/w) of chemical impurities.

Depending on which other solid state forms comparison is made with, the solid state forms of Eluxadoline of the present invention have advantageous properties selected from at least one of the following: chemical purity, flowability, solubility, dissolution rate, morphology or crystal habit, stability—such as chemical stability as well as thermal and mechanical stability with respect to polymorphic conversion, stability towards dehydration and/or storage stability, low content of residual solvent, a lower degree of hygroscopicity, flowability, and advantageous processing and handling characteristics such as compressibility, and bulk density.

A solid state form, such as a crystal form or amorphous form, may be referred to herein as being characterized by graphical data "as depicted in" or "as substantially depicted in" a Figure. Such data include, for example, powder X-ray diffractograms and solid state NMR spectra. As is well-known in the art, the graphical data potentially provides additional technical information to further define the respective solid state form (a so-called "fingerprint") which cannot necessarily be described by reference to numerical values or peak positions alone. In any event, the skilled person will understand that such graphical representations of data may be subject to small variations, e.g., in peak relative intensities and peak positions due to certain factors such as, but not limited to, variations in instrument response and variations in sample concentration and purity, which are well known to the skilled person. Nonetheless, the skilled person would readily be capable of comparing the graphical data in the Figures herein with graphical data generated for an unknown crystal form and confirm whether the two sets of graphical data are characterizing the same crystal form or two different crystal forms. A crystal form of a Eluxadoline referred to herein as being characterized by graphical data "as depicted in" or "as substantially depicted in" a Figure will thus be understood to include any crystal forms of Eluxadoline characterized with the graphical data having such small variations, as are well known to the skilled person, in comparison with the Figure.

As used herein, the term "isolated" in reference to a solid state form of Eluxadoline of the present invention corresponds to a solid state form of Eluxadoline that is physically separated from the reaction mixture in which it is formed.

As used herein, unless stated otherwise, the XRPD measurements are taken using copper Kα radiation wavelength 1.5418 Å.

As used herein, particle size distribution measurements were obtained by laser diffraction method, using n-hexane dispersant. Preferably, the dilution medium is dioctyl sulfosuccinate sodium salt (DSSS) in hexane (more preferably 0.2% w/v DSSS in hexane). Preferably the dispersion is sonicated for 15 seconds, by external ultrasound.

A thing, e.g., a reaction mixture, may be characterized herein as being at, or allowed to come to "room temperature" or "ambient temperature", often abbreviated as "RT." This means that the temperature of the thing is close to, or the same as, that of the space, e.g., the room or fume hood, in which the thing is located. Typically, room temperature is from about 20° C. to about 30° C., or about 22° C. to about 27° C., or about 25° C.

The amount of solvent employed in a chemical process, e.g., a reaction or crystallization, may be referred to herein as a number of "volumes" or "vol" or "V." For example, a material may be referred to as being suspended in 10 volumes (or 10 vol or 10V) of a solvent. In this context, this expression would be understood to mean milliliters of the solvent per gram of the material being suspended, such that suspending 5 grams of a material in 10 volumes of a solvent means that the solvent is used in an amount of 10 milliliters of the solvent per gram of the material that is being suspended or, in this example, 50 mL of the solvent. In another context, the term "v/v" may be used to indicate the number of volumes of a solvent that are added to a liquid mixture based on the volume of that mixture. For example, adding solvent X (1.5 v/v) to a 100 ml reaction mixture would indicate that 150 mL of solvent X was added.

A process or step may be referred to herein as being carried out "overnight." This refers to a time interval, e.g., for the process or step, that spans the time during the night, when that process or step may not be actively observed. This time interval is from about 8 to about 20 hours, or about 10-18 hours, typically about 16 hours.

As used herein, the term "reduced pressure" refers to a pressure that is less than atmospheric pressure. For example, reduced pressure may be about 10 mbar to about 100 mbar.

As used herein, and unless stated otherwise, the term "anhydrous" in relation to crystalline Eluxadoline relates to a crystalline Eluxadoline which does not include any crystalline water (or other solvents) in a defined, stoichiometric amount within the crystal. Moreover, an "anhydrous" form does not contain more than 1% (w/w) of either water or organic solvents as measured for example by TGA or GC.

As used herein, and unless indicated otherwise, the terms "wet crystalline form" or "wet form" refer to a polymorph that was not dried using any conventional techniques to remove residual solvent. Examples for such conventional techniques can be, but not limited to, evaporation, vacuum drying, oven drying, drying under nitrogen flow etc.

As used herein, and unless indicated otherwise, the terms "dry crystalline form" or "dry form" refer to a polymorph that was dried using any conventional techniques to remove residual solvent. Examples for such conventional techniques can be, but not limited to, evaporation, vacuum drying, oven drying, drying under nitrogen flow etc.

Figure 3:
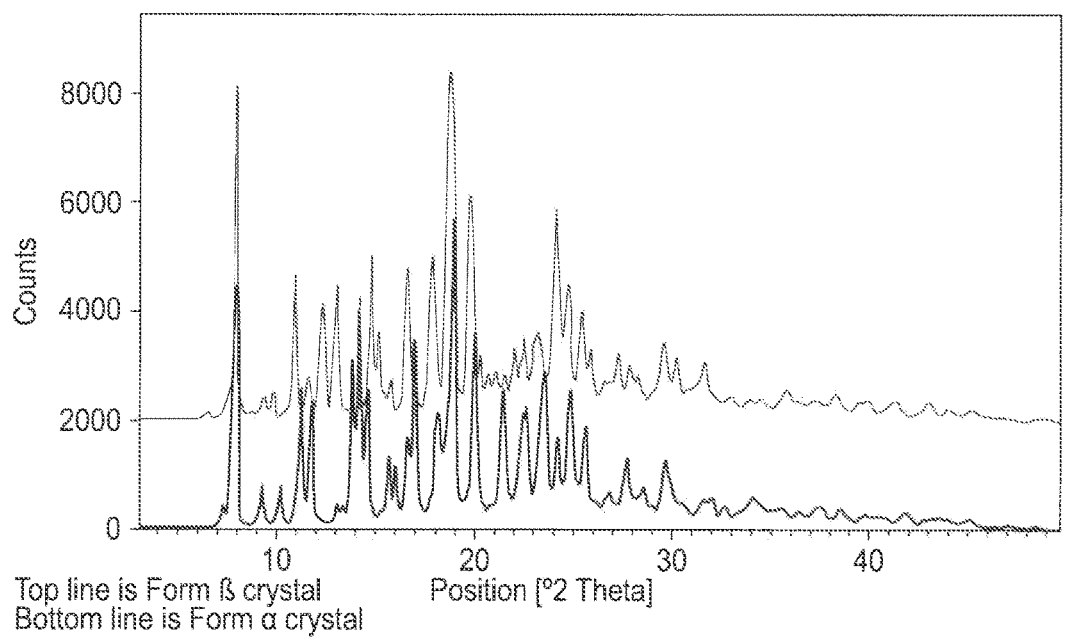
FIG. 3 shows X-ray powder diffractograms of Eluxadoline forms alpha and beta (as described in U.S. Pat. No. 8,691,860).

As used herein, and unless indicated otherwise, the term crystalline Eluxadoline form alpha, or form alpha or Eluxadoline form alpha refers to the crystalline form alpha as described in U.S. Pat. No. 8,691,860. According to this patent, form alpha is characterized by a powder X-ray diffraction pattern having powder X-ray diffraction peaks at about 10.2, 11.3, 11.8, 14.0, 14.3, 14.7, 16.1 and 18.3 degrees 2-theta. A powder X-ray diffraction pattern according to this patent is shown in FIG. 3 (bottom line).

The present invention also describes form alpha which is characterized by a powder X-ray diffraction pattern having peaks at 8.0, 11.3, 14.3, 17.1 and 20.1±0.2 degrees two-theta. Form alpha described in the present invention can be further characterized by a powder X-ray diffraction pattern having peaks at 9.4, 10.2, 11.3, 14.7 and 19.1 degrees two-theta ±0.2 degrees two-theta. As used herein, and unless indicated otherwise, the term crystalline Eluxadoline form beta, or form beta or Eluxadoline form beta refers to the crystalline form beta as described in U.S. Pat. Nos. 8,691,860 or 7,994,206. According to the '206 patent, form beta is characterized by a powder X-ray diffraction pattern having powder X-ray diffraction peaks at about 11.0, 12.4, 14.9, 15.2, 22.1, 25.6, 27.4, and 30.4 degrees 2-theta. A powder X-ray diffraction pattern according to this patent is shown in FIG. 3 (top line).

Figure 2:
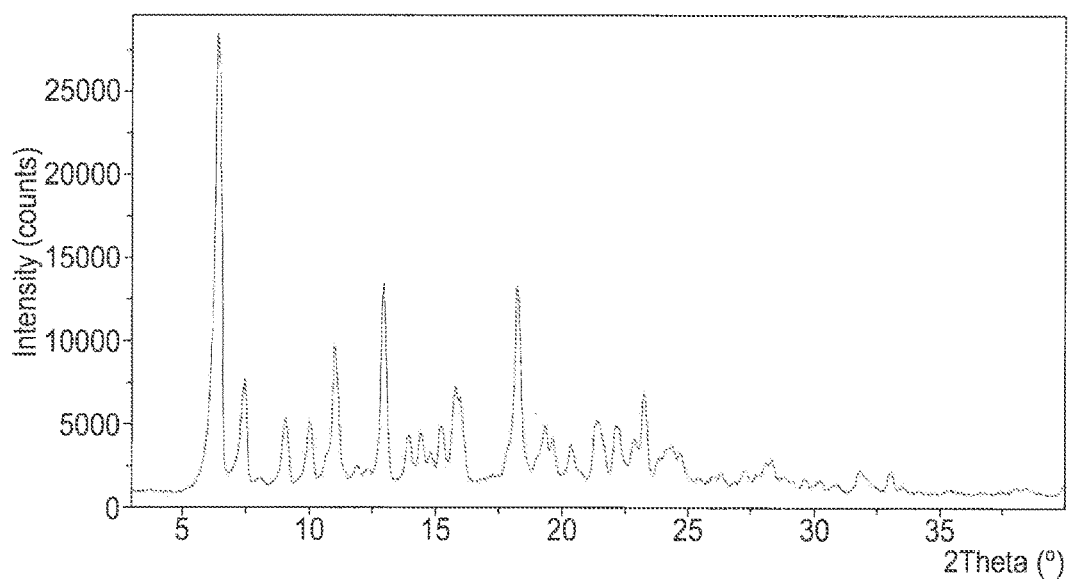
FIG. 2 shows an X-ray powder diffractogram of Eluxadoline form I.

In one embodiment, the present invention comprises crystalline Eluxadoline, designated form I, characterized by data selected from one or more of the following: X-ray powder diffraction pattern having peaks at about 6.4, 7.5, 9.1, 10.0 and 13.0 degrees two theta ±0.2 degrees two theta; an X-ray powder diffraction pattern as depicted in FIG. 2; and combinations of this data.

Crystalline form I of Eluxadoline can be further characterized by the X-ray powder diffraction pattern having peaks at 6.4, 7.5, 9.1, 10.0 and 13.0 degrees two theta ±0.2 degrees two theta and also having any one, any two, any three or more additional peaks selected from 11.0, 12.0, 14.4, 15.8 and 18.3±0.2 degrees two theta ±0.2 degrees two theta.

Crystalline form I of Eluxadoline may be characterized by each of the above characteristics alone and/or by all possible combinations. Crystalline form I of Eluxadoline may be a THF solvate.

The present invention describes amorphous Eluxadoline. The amorphous form may be characterized by a typical amorphous "halo" XRD pattern; an X-ray powder diffraction pattern as depicted in FIG. 1; and combinations of this data.

Figure 4:
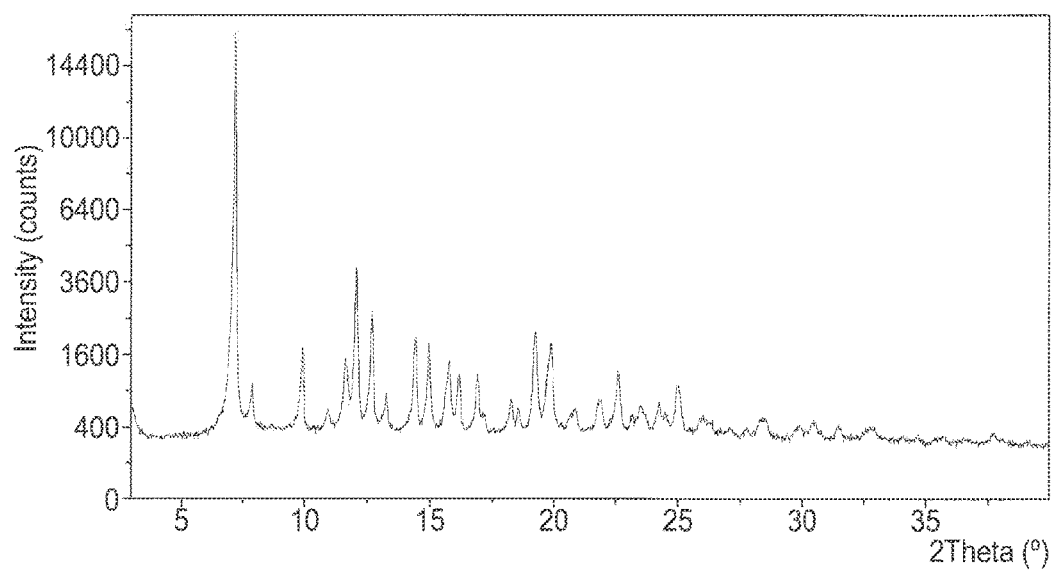
FIG. 4 shows an X-ray powder diffractogram of Eluxadoline form II.

In another embodiment, the present invention comprises crystalline form II of Eluxadoline, designated Form II, characterized by data selected from one or more of the following: an X-ray powder diffraction pattern having peaks at 7.2, 11.6, 12.1, 12.7 and 16.9 degrees two theta ±0.2 degrees two theta; an X-ray powder diffraction pattern as depicted in FIG. 4; and combinations of these data.

Crystalline Form II of Eluxadoline may be further characterized by X-ray powder diffraction pattern having peaks at: at 7.2, 11.6, 12.1, 12.7 and 16.9 degrees two theta ±0.2 degrees two theta and also having one, two, three, four or five peaks selected from: 9.9, 14.4, 14.9, 19.2 and 19.9 degrees two theta±0.2 degrees two theta.

Without wishing to be bound by theory, it is believed that form II may be a hydrate or mixture of water with methanol in a crystal structure. Form II may also be a methanol solvate. Crystalline form II of Eluxadoline may be characterized by each of the above characteristics alone and/or by all possible combinations. Crystalline form II of the present invention can be used to prepare other polymorphs of Eluxadoline, particularly crystalline form alpha in a stable form, as defined herein below.

The above solid state forms of Eluxadoline may be obtained either as a wet form, or a dry form.

Crystalline Forms I and II of Eluxadoline can be used in the preparation of Eluxadoline form alpha as described herein. The crystalline forms I and II can be prepared from amorphous Eluxadoline as described herein, and then subsequently converted to form alpha by drying as described herein.

The present invention describes amorphous Eluxadoline. In preferred embodiments, the present invention comprises amorphous Eluxadoline in a stable form. The stable amorphous form of the present invention essentially does not convert to crystalline Eluxadoline in various conditions, i.e., contains not more than ("NMT") 10% (w/w) of any crystalline form, for example form beta or form alpha. According to one embodiment of the invention, amorphous Eluxadoline contains not more than 10% (w/w) of any crystalline form, and preferably no detectable amount of any crystalline form, when stored at 25° C. and at the following conditions:

0% relative humidity for 3 days, preferably for 7 days, or
20% relative humidity for 3 days, preferably for 7 days, or
40% relative humidity for 3 days, preferably for 7 days, or
60% relative humidity for 3 days, preferably for 7 days, or
80% relative humidity for 3 days, preferably for 7 days, or
100% relative humidity for 3 days, preferably for 7 days.

In another embodiment, amorphous Eluxadoline according to the invention does not convert to crystalline Eluxadoline under conditions of 0-100% relative humidity at 25° C. for 7 days. Alternatively, the stable amorphous Eluxadoline contains not more than 10% (w/w), and preferably no detectable amount, of any crystalline form when stored at 25° C. and 60% relative humidity (RH) for 3 days preferably for 7 days. Preferably, the stable amorphous Eluxadoline according to an embodiment of the invention contains not more than 10% (w/w), and preferably no detectable amount, of any crystalline form, when stored at 25° C. and 80% relative humidity (RH) for 3 days, preferably for 7 days. In another embodiment, the amorphous Eluxadoline contains not more than 5%, preferably no detectable amount, of any crystalline form, when exposed to 0-100% relative humidity at 25° C. for 7 days, or contains not more than 5%, preferably no detectable amount, of any crystalline form, when exposed to 0-100% relative humidity at 25° C. for 30 days, or not more than 5%, preferably no detectable amount, of any crystalline form, when exposed to 0-100% relative humidity at 25° C. for 60 days.

The content of crystalline form in the amorphous form is typically measured by any suitable method appreciated by a person skilled in the art, for example PXRD, solid-state NMR, IR, Raman, or DSC. For example, a skilled person may measure the content of form alpha or form beta using PXRD. Accordingly, the content of crystalline Eluxadoline form alpha or form beta in amorphous Eluxadoline will be measured by detecting and quantifying the described characteristic peaks of form alpha or form beta. The characteristic peaks of crystalline Eluxadoline form beta used for the above described measurement can be selected from the following list of peaks at about: 11.0, 12.4 and 15.2 degrees two theta ±0.2 degrees two theta. The characteristic peaks of crystalline Eluxadoline form alpha used for the above described measurement can be selected from the following list of peaks at about 10.2, 11.3, 11.8, 14.0, 14.3, 14.7 degrees two theta ±0.2 degrees two theta.

In specific embodiments, the stable amorphous Eluxadoline contains not more than 10% (w/w) of any crystalline form when stored at 60% relative humidity ("RH") for 3 days, preferably for 7 days. More preferably, the stable amorphous Eluxadoline contains not more than 10% (w/w) of any crystalline form when stored at 80% relative humidity ("RH") for 3 days, preferably for 7 days. More preferably, the stable amorphous Eluxadoline contains not more than 10% (w/w) of any crystalline form when stored at the conditions specified in Table 2 herein below.

In particularly preferred embodiment, the present invention comprises amorphous Eluxadoline in highly pure and stable form. The highly pure and stable amorphous form typically has HPLC purity of at least 99% (w/w), preferably at least 99.2% (w/w), and it does not convert to crystalline form as described herein above. Hence, the amorphous Eluxadoline of the present invention can be in a high chemical purity, as well as a high polymorphic purity. The highly pure and stable amorphous Eluxadoline contains not more than 10% (w/w) of any crystalline form when stored at the conditions specified in Table 2 herein below. In particular, amorphous Eluxadoline is surprising highly stable, showing no polymorphic conversion to crystalline forms under rigorous conditions of high relative humidity and high temperature.

Amorphous Eluxadoline of the present invention exhibits an irregular particle shape.

Figure 10:
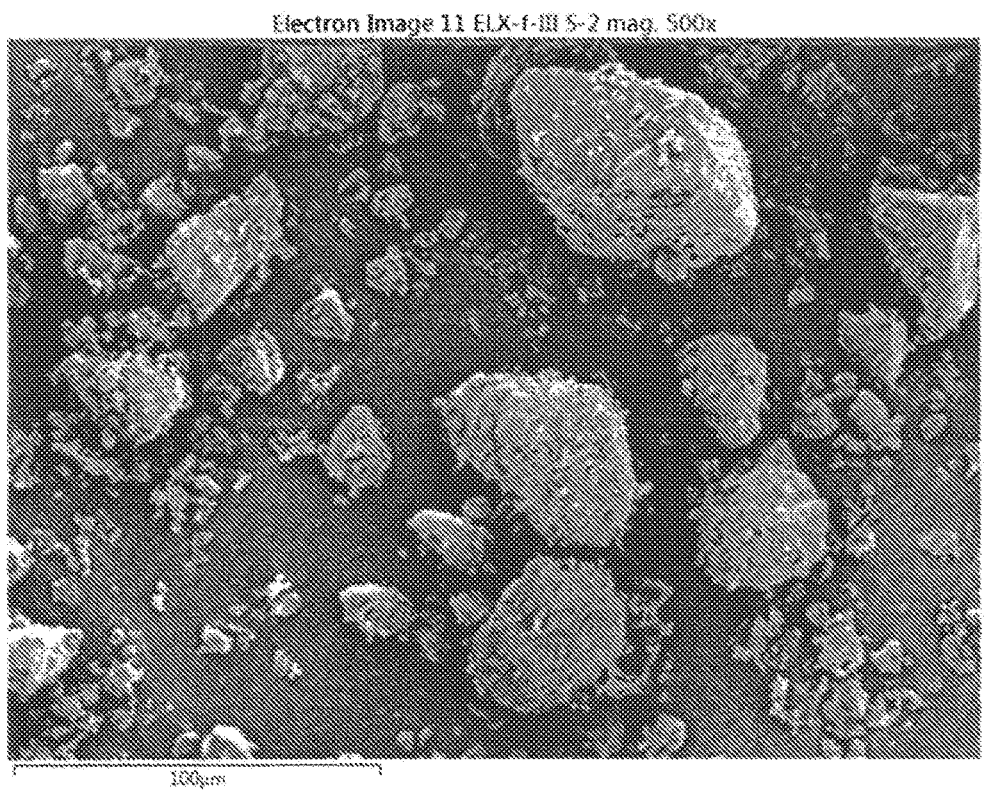
FIG. 10: SEM image of stable Amorphous Eluxadoline prepared according to Example 20.

The amorphous Eluxadoline of the present invention may have a particle size distribution of d(0.9) of from 100-250 µm. In another embodiment, the amorphous Eluxadoline may have a particle size distribution of: d (0.1)=1-4 µm, d(0.5)=15-25 µm and d(0.9)=100-250 µm. Advantageously, the amorphous Eluxadoline can have a high dissolution and solubility. For example, the amorphous Eluxadoline can have a dissolution of greater than about 85%, greater than about 90%, or greater than about 94%, after 60 minutes at 37° C. in 50 mM phosphate buffer at pH 6.8. The solubility of the amorphous Eluxadoline according to the invention is also high: about 3 to about 10 mg/ml, about 3 to about 8 mg/ml, or about 4 to about 6 mg/ml at 37° C. in 50 mM phosphate buffer at pH 2 and/or pH 6.8, or about 6 to about 15 mg/ml, about 7 to about 12 mg/ml, or about 8 to about 10 mg/ml at 37° C. in 50 mM phosphate buffer at pH 4. Amorphous Eluxadoline may have a particle morphology substantially according to FIG. 10.

Amorphous Eluxadoline according to the invention can be prepared by drying isolated amorphous Eluxadoline under reduced pressure or a vacuum, preferably wherein the drying is at a temperature range of: about 30° C. to about 75° C., about 35° C. to about 70° C., or about 40° C. to about 75° C. The drying may be continued to a loss on drying of about 2 to about 7 wt %, about 3 to about 6 wt % or about 5 wt %.

Amorphous Eluxadoline according to the present invention can also be prepared having a larger particle size distribution, i.e. d (0.1)=6-12 µm, d(0.5)=80-50 µm and d(0.9)=100-250 µm, or having a specific surface area of: about 0.8 m$^2$/g to about 1.6 m$^2$/g, about 1.0 m$^2$/g to about 1.4 m$^2$/g, or about 1.1 m$^2$/g to about 1.3 m$^2$. This form of Eluxadoline can be in the form of a free flowing powder, having good flowability properties, for example having a flow function value of greater than about 10, about 10 to about 16, about 11 to about 14, about 11 to about 13, preferably as measured according to ASTM standard D 6128-16 (Standard Test Method for Shear Testing of Bulk Solids Using the Jenike Shear Tester). According to Jenike A W. (1964). Storage and flow of solids. Utah. Eng Exp Station Bull, 123:1-194, the classification of flow type according to flow function value is as follows:

| Type of flow | Flow Function Value |
| --- | --- |
| Free-flowing | 10 < FF |
| Easy-flowing | 4 < FF < 10 |
| Cohesive | 2 < FF < 4 |
| Very cohesive and non-flowing | FF < 2 |

Figure 11:
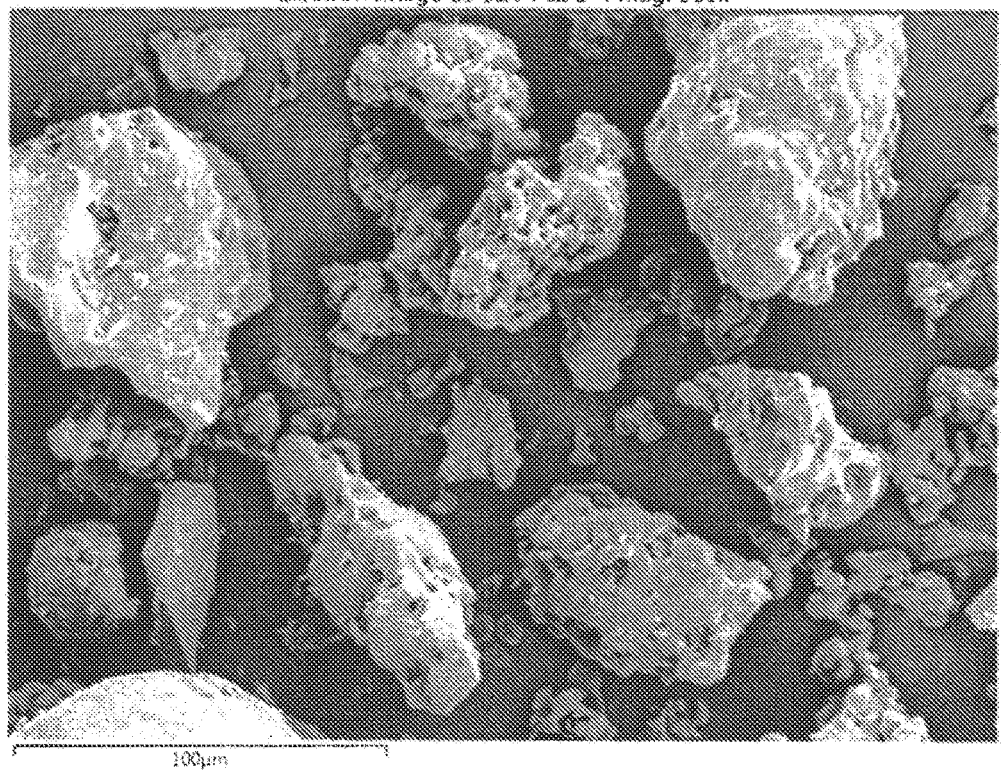
FIG. 11: SEM image of stable Amorphous Eluxadoline prepared according to Example 21.
Figure 12:
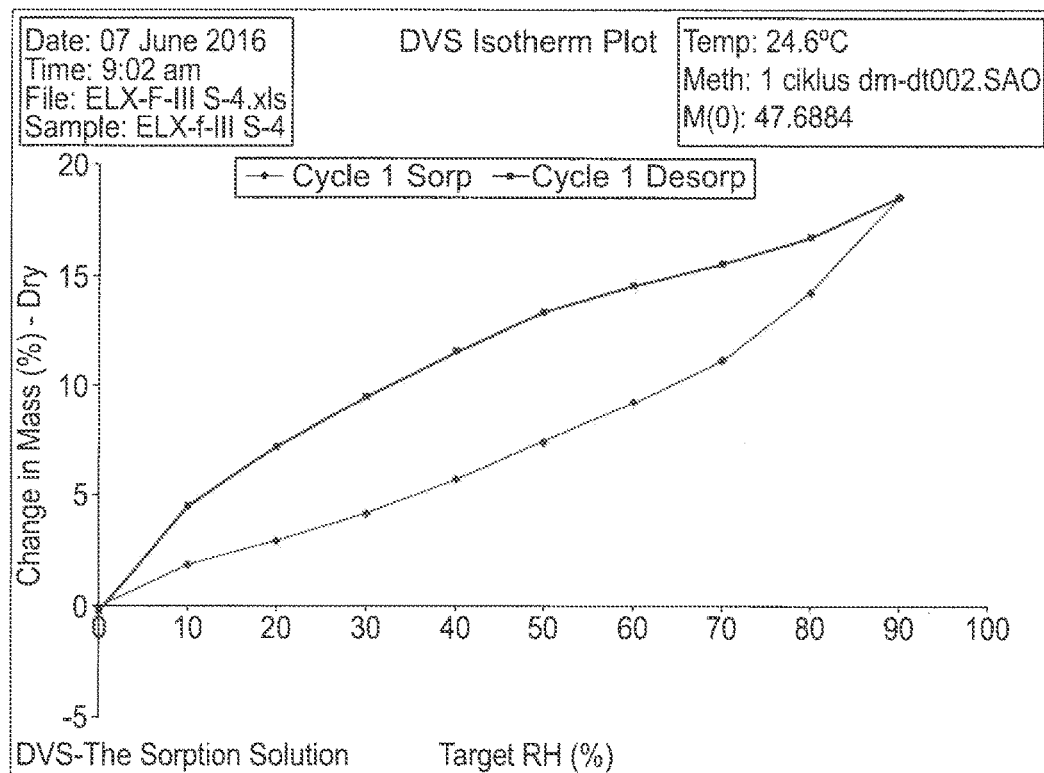
FIG. 12: DVS isotherm of stable Amorphous Eluxadoline prepared according to Example 21.

The particle morphology of the amorphous Eluxadoline according to this embodiment of the present invention is substantially as depicted in FIG. 11. The amorphous Eluxadoline can be prepared by a process comprising washing amorphous form with water, and drying. The drying is preferably conducted in at least two stages: (a) drying, preferably in a fluidized bed dryer, at a temperature of about 35° C. to about 55° C., about 35° C. to about 45° C., about 40 to about 50° C., or about 45° C.; and (b) further drying, preferably in a vacuum tray drier at a temperature of about 35° C. to about 55° C., about 35° C. to about 45° C., about 40 to about 50° C., or about 45° C. The drying in step (a) is to a loss on drying of about 5 to about 12 wt %, about 6 to about 10 wt %, about 7 to about 9 wt % or about 8 wt %. The drying in step (b) is to a loss on drying of about 1 to about 5 wt %, about 1.5 to about 4 wt %, about 1.5 to about 3.5 wt % or about 2 to about 2.5 wt %.

The amorphous Eluxadoline starting material can be prepared by a process comprising: (a) reacting an alkyl ester, preferably a $C_1$-$C_6$ alkyl ester, and more preferably a methyl ester, of Eluxadoline with a base in the presence of a solvent comprising water, and (b) isolating amorphous Eluxadoline from the reaction mixture. The solvent is preferably an organic solvent and water, preferably a water-miscible ether and water, and more preferably, THF and water.

In the above processes, the base in step (a) is preferably an inorganic base, preferably an alkali or alkaline earth metal hydroxide, more preferably an alkali metal hydroxide, most preferably sodium hydroxide or potassium hydroxide, and particularly sodium hydroxide.

After step (a), the pH of the reaction mixture is adjusted to about 6.0 to about 7.5 about 6.0 to about 7.2, or about 6.4 to about 7.0, to obtain the zwitterion form of Eluxadoline.

Any suitable acid can be used for the pH adjustment— preferably, however, the pH is adjusted with a mineral acid, preferably selected from hydrochloric acid, hydrobromic acid, sulphuric acid, nitric acid or phosphoric acid, preferably hydrochloric acid, hydrobromic acid, sulphuric acid, and most preferably hydrochloric acid.

Preferably, the solvent is water.

The reaction mixture is preferably cooled prior to step (b), following which the amorphous Eluxadoline may be isolated, e.g. by filtration.

The above described solid state forms of Eluxadoline can be used to prepare other solid state forms of Eluxadoline; or other salts of Eluxadoline and their solid state forms. The present invention further provides solid state forms of Eluxadoline for use in the preparation of other solid state forms of Eluxadoline, or other salts of Eluxadoline and their solid state forms, in particular Eluxadoline form alpha, beta, form I, II, III or IV.

Particularly, the present invention comprises the above described amorphous form of Eluxadoline, preferably stable amorphous form, more preferably highly pure and stable amorphous form, for use in the preparation of crystalline form alpha, crystalline form I and crystalline form II. The present inventions also comprise the above described form I and form II of Eluxadoline for use in the preparation of Eluxadoline form alpha.

In another embodiment the present invention comprises a process for preparing form alpha. The process comprises heating form I to a temperature of about 100° C. to about 140° C. Optionally, the process can be done under vacuum. If vacuum is applied, heating can be done to lower temperature, for example to at least about 40° C. Alternatively, form alpha can be obtained by drying crystalline form II for about 16 h at 60° C. at 10 mbar.

Figure 6:
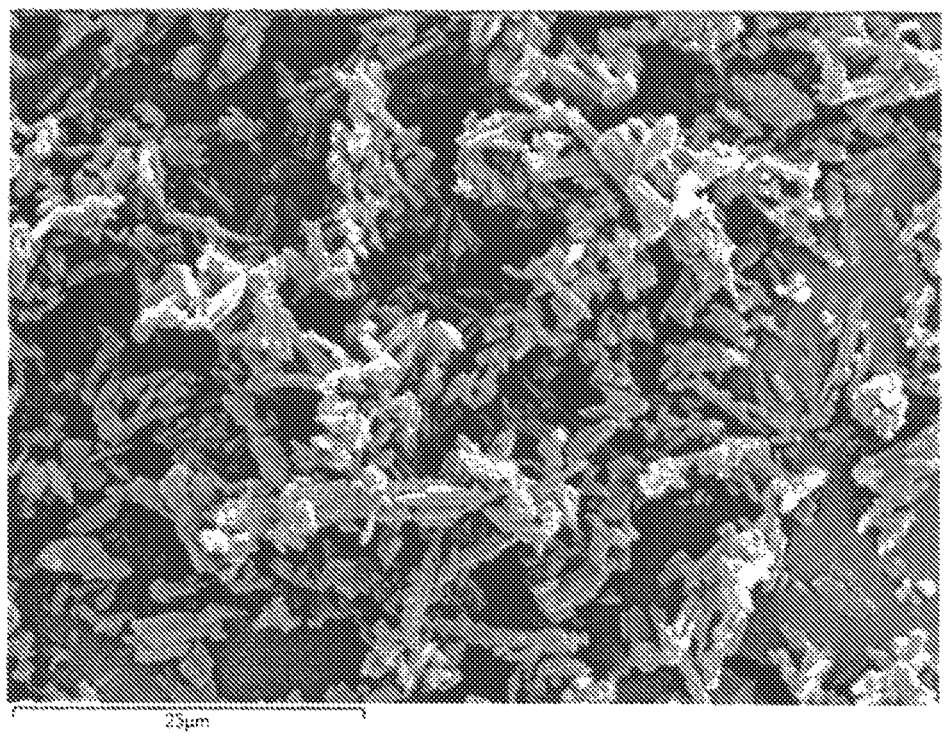
FIG. 6 shows an SEM image of stable form alpha (obtained from methanol).

In a further aspect of the present invention, there is provided a crystalline form alpha of Eluxadoline, which is characterized by a powder X ray diffraction pattern having peaks at 8.0, 11.3, 14.3, 14.7, 17.1 and 20.1±0.2 degrees two-theta, having at least one of the following:
   (i) a TGA thermogram showing a weight loss step between 25° C. and 121° C. of up to 1.3%, and preferably of 1 to 1.3%;
   (ii) an SEM image as depicted in FIG. 6;
   (iii) stability to conversion to any other solid state forms of Eluxadoline, and preferably stability to conversion to Eluxadoline hydrate, or form beta, at 0-100% RH at 25° C. for 3 days, preferably for 7 days and more preferably for 21 days;
   (iv) chemical stability and polymorphic stability to conversion to any other solid state form by heating at 50° C., and 100° C. for 3 h;
   (v) stability to conversion to any other solid state form of Eluxadoline and preferably stability to conversion to Eluxadoline hydrate, or form beta, at: 40° C./75% RH for 30 days; 50° C. for 30 days; or 50° C./80% RH for 30 days and/or
   (vi) a combination of any two or more of (i)-(v).

The form alpha may be further characterized by powder X-ray diffraction pattern having peaks at 9.4, 10.2, 11.3, 14.7 and 19.1 degrees two-theta ±0.2 degrees two-theta. The crystalline Eluxadoline form alpha according to the invention may be characterized by a powder X-ray diffraction pattern having peaks at: 8.0, 9.4, 10.2, 11.3, 11.8, 13.2, 14.0, 14.3, 14.7, 15.8, 16.1, 17.1, 19.1, 20.1, 21.6, 22.8, 23.8, 24.5, 25.1 and 25.9 degrees two-theta ±0.2° two-theta, and at least one of (i), (ii) or (iii) or a combination of two or more of (i), (ii) and (iii).

Figure 5:
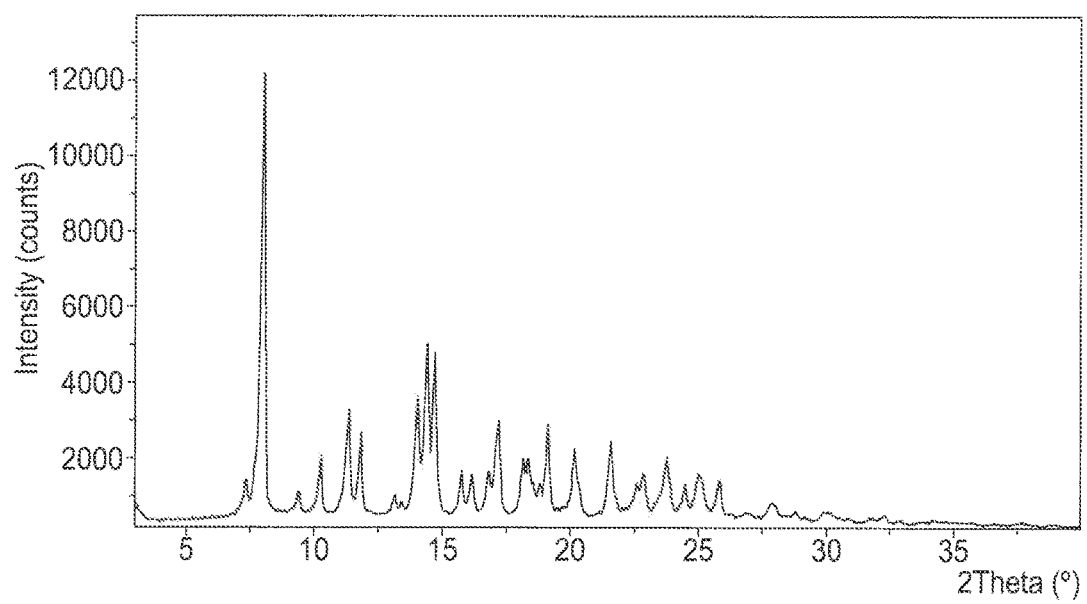
FIG. 5 shows an X-ray powder diffractogram of stable form alpha (obtained from methanol).
Figure 13:
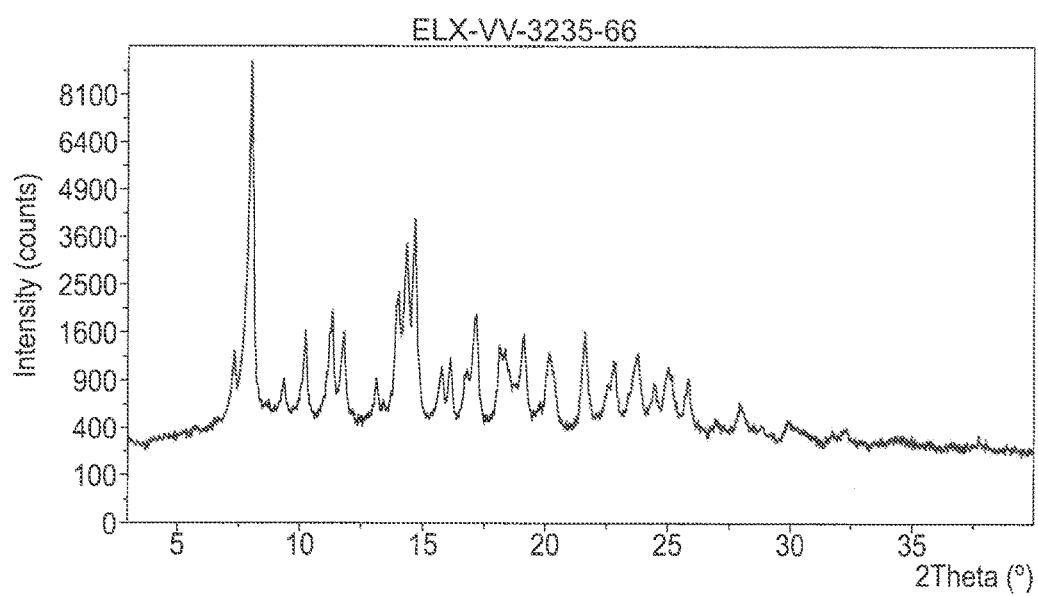
FIG. 13: X-ray powder diffractogram of stable form alpha of Example 19.
Figure 16:
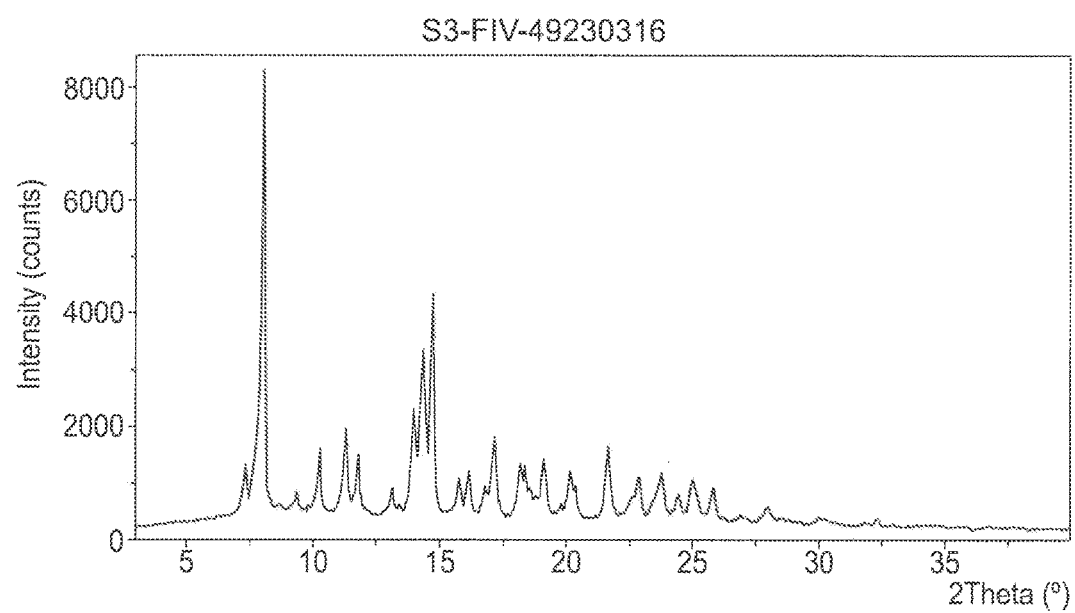
FIG. 16: X-ray powder diffractogram of stable form alpha of Example 22.

Crystalline Eluxadoline form alpha according to the invention can be characterised by a powder XRD pattern as depicted in any of FIG. 5, FIG. 13 or FIG. 16, and preferably FIG. 13 or FIG. 16.

Figure 17:
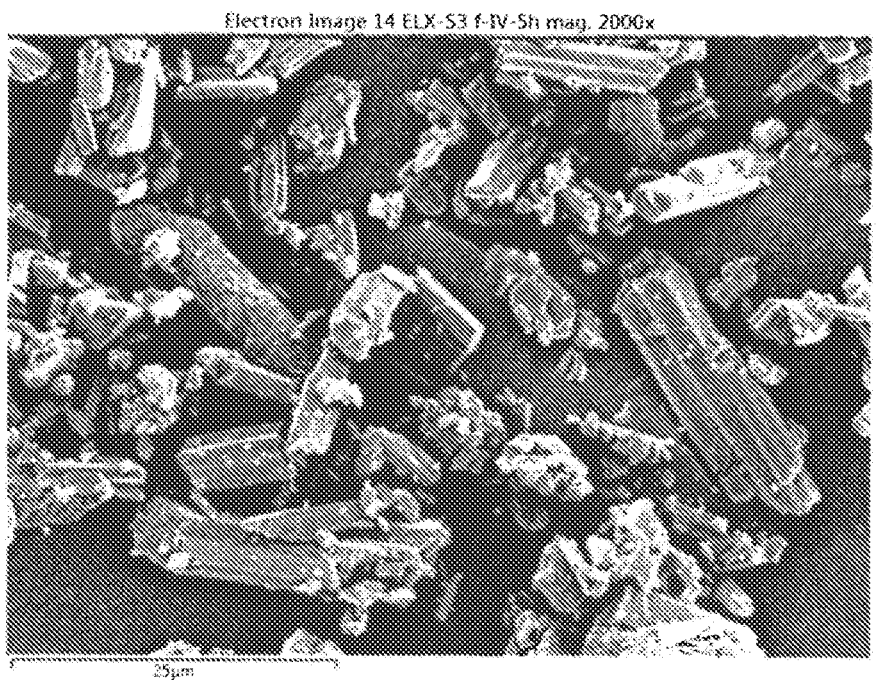
FIG. 17: SEM image of stable Eluxadoline form alpha prepared according to Example 22.
Figure 18:
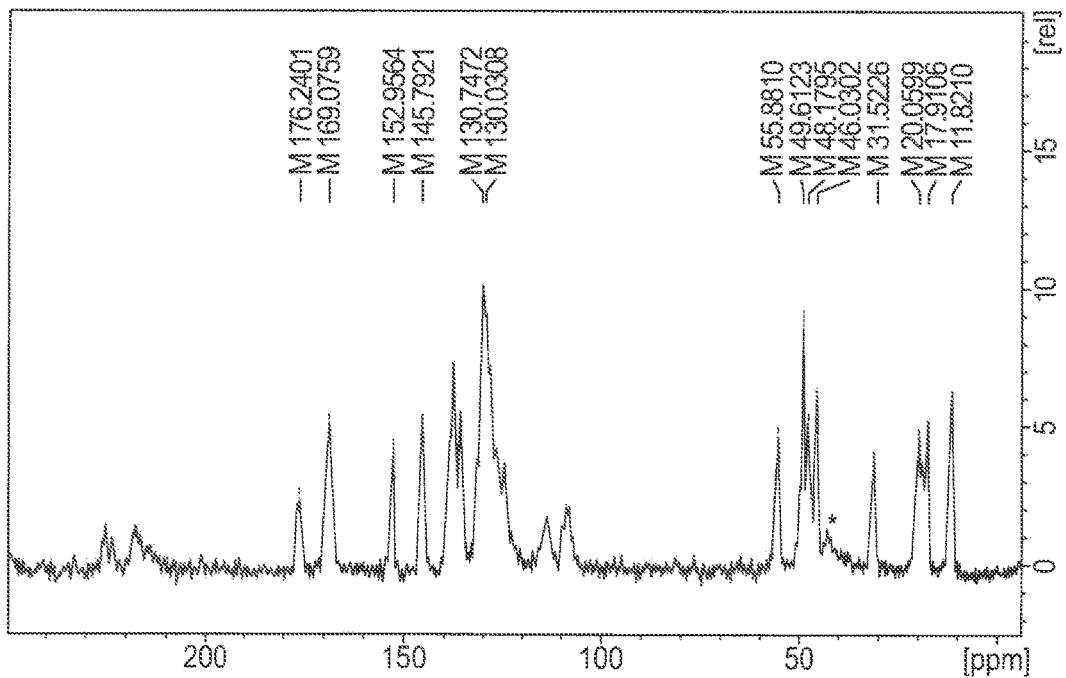
FIG. 18: $^{13}C$ solid state NMR for Eluxadoline Form alpha from Example 19.
Figure 20:
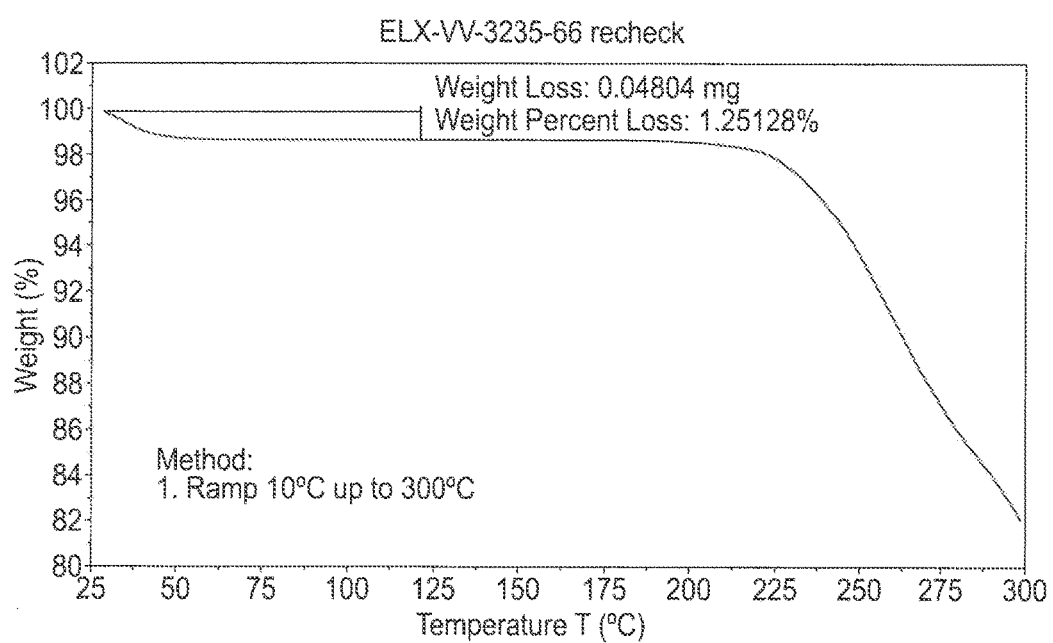
FIG. 20: TGA Thermogram of Eluxadoline Form alpha from Example 19.
Figure 22:
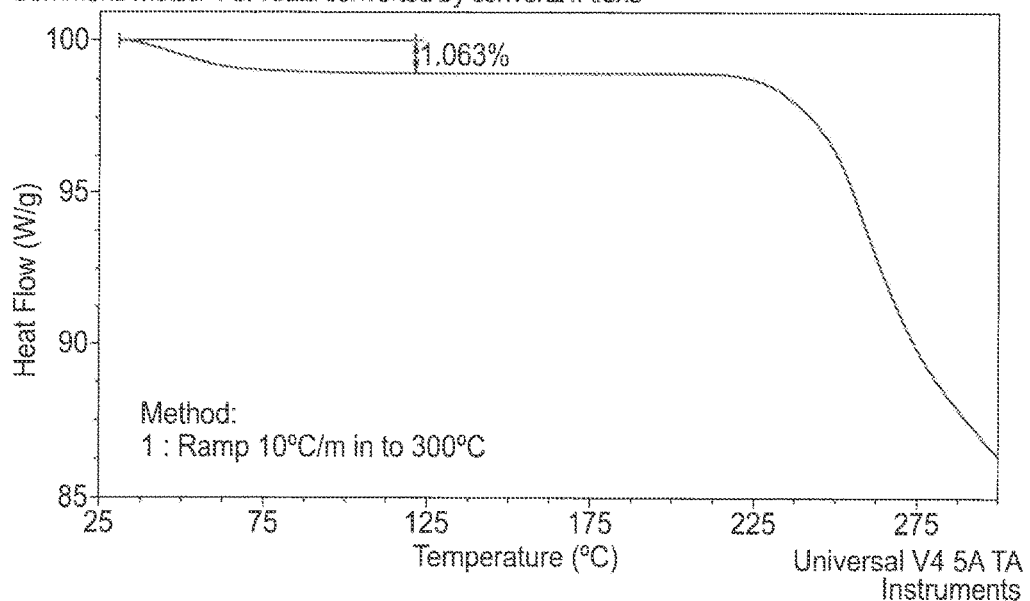
FIG. 22: TGA Thermogram of Eluxadoline Form alpha from Example 22.

Alternatively, or additionally, crystalline Eluxadoline form alpha can be characterized by having a solid state $^{13}$C NMR having peaks at 176.2, 169.1, 153.0, 145.8, 130.8, ±0.2 ppm, or a solid state $^{13}$C NMR spectrum having chemical shift differences between a reference peak at 55.9±0.2 ppm of: 120.3, 113.2, 97.1, 89.9, 74.9±0.1 ppm respectively; or by a solid state $^{13}$C NMR spectrum substantially as depicted in FIG. 18; or by a combination thereof. Advantageously, the crystalline form alpha is stable, and preferably does not convert to more than 5% of any other crystalline or amorphous form when exposed to 0-100% relative humidity for: 8, 14 or 21 days at 25° C. The crystalline form alpha may have a rod-like morphology (for example substantially as depicted in FIG. 14 or FIG. 17). The crystalline Eluxadoline form alpha can have a TGA thermogram substantially as depicted in FIG. 20 or FIG. 22. Crystalline Eluxadoline form alpha may be a hydrate, preferably having a water content of up to 1.3 wt % and preferably 1-1.3 wt % by TGA).

Crystalline Eluxadoline form alpha according to an embodiment of the present invention may be characterised by a powder x-ray diffraction pattern having peaks at: 8.0, 9.4, 10.2, 11.3, 11.8, 13.2, 14.0, 14.3, 14.7, 15.8, 16.1, 17.1, 19.1, 20.1, 21.6, 22.8, 23.8, 24.5, 25.1 and 25.9 degrees two-theta ±0.2° two-theta and a TGA thermogram showing a weight loss step between 25° C. and 121° C. of up to 1.3%, and preferably of 1 to 1.3%, preferably having a TGA thermogram substantially according to FIG. 20 or 22. The crystalline Eluxadoline form alpha can have a bulk density of about 0.18 to about 0.40, about 0.2 to about 0.36, about 0.30 to about 0.35, or about 0.33 mg/mm$^3$, and/or a tapped density of: about 0.20 to about 0.45, about 0.30 to about 0.42, about 0.35 to about 0.42, or about 0.39 mg/mm$^3$. The crystalline Eluxadoline form alpha of this embodiment preferably has a Carr index of less than about 27, preferably less than about 20. Crystalline form alpha may have a flow function of greater than about 2.3, preferably as measured according to ASTM standard D 6128-16.

Crystalline Eluxadoline form alpha may have a density at 0.2 Mpa, of: about 0.43 to about 0.52, preferably about 0.52 mg/mm$^3$.

Crystalline Eluxadoline form alpha according to this embodiment may have a particle size distribution of D10 of about 1 μm to about 5 μm; a D50 or about 5 μm to about 15 μm and D90¬ of about 20 μm to about 40 μm, or a particle size distribution of D10 of about 3 μm to about 4 μm; a D50 or about 8 μm to about 12 μm and D90¬, of about 24 μm to about 31 μm.

The crystalline Eluxadoline form alpha advantageously exhibits a high dissolution and high specific surface area (for example about 4 to about 12 m$^2$/g, preferably about 9 to about 10 m$^2$/g). Thus, the crystalline Eluxadoline form alpha can have a dissolution of greater than about 90%, greater than about 92%, greater than about 94%, or greater than about 96%, after 30 minutes at 37° C. in phosphate buffer at pH 6.8, and preferably 99% after 20 minutes at 37° C. in phosphate buffer pH 6.8. Crystalline form alpha of the present invention can be prepared by a process which comprises drying a solvate form of Eluxadoline, wherein the solvate is with an organic solvent. The starting solvate form of Eluxadoline can be prepared by a process comprising: (a) combining amorphous Eluxadoline with the organic solvent to form a mixture; (b) heating the mixture; and (c) cooling the heated mixture. The solvate form of Eluxadoline is preferably a $C_1$-$C_6$ alcohol solvate (preferably methanol solvate), or a $C_2$-$C_6$ alkyl or $C_4$-$C_6$ cyclic alkyl ether (preferably a tetrahydrofuran solvate). Step (b) is preferably conducted at a temperature of: about 40° C. to about 78° C., about 45° C. to about 70° C., or about 45 to about 60° C. Step (c) is preferably conducted at a temperature of: about −10° C. to about 20° C., about −5° C. to about 10° C., or about 0° C. to about 5° C.

In one embodiment, crystalline form alpha of the present invention can be prepared by a process which comprises drying Eluxadoline methanol solvate. Preferably, the process comprises: (a) dissolving Eluxadoline in an organic solvent comprising methanol to form a solution; (b) crystallising Eluxadoline methanol solvate from the solution; and (c) drying to obtain crystalline form alpha. Typically, step (a) is carried at a temperature of: about 10° C. to about 20° C., about −10° C. to about 18° C., about −5° C. to about 15° C. or about −5° C. to about 10° C. Step (b) preferably comprises: (b1) heating the solution, and (b2) cooling the heated solution, wherein step (b1) is carried out at a temperature of: about 20° C. to about 80° C., about 25° C. to about 65° C., or about 50° C. to about 65° C. Step (b2) is preferably conducted at a temperature of: about −10° C. to about 20° C., about −5° C. to about 10° C., or about 0° C. to about 5° C. Step (c) is preferably carried out at a temperature of: about 20° C. to about 80° C., about 22° C. to about 70° C., or about 40° C. to about 60° C., preferably under reduced pressure or vacuum. Advantageously, the methanol solvate has a low desolvation temperature (up to about 60° C.), which enables facile solvent removal from the crystal structure, thereby producing the Eluxadoline form alpha product having a high HPLC and a residual methanol content below the quantification limit. Moreover, the obtained Eluxadoline form alpha is strikingly stable to high relative humidity as well as elevated temperatures, or a combination of high relative humidity and elevated temperatures for prolonged periods. Eluxadoline form alpha also exhibits excellent dissolution and solubility, which facilitates formulation processes.

Alternatively, form alpha can be prepared by drying Eluxadoline THF solvate, comprising: (a) combining amorphous Eluxadoline in an organic solvent comprising THF to form a slurry; (b) crystallising Eluxadoline THF solvate from the solution; and (c) drying to obtain crystalline form alpha. Step (a) may further comprise heating the slurry to a temperature of: about 30° C. to about 80° C., about 40° C. to about 60° C. or about 45° C. to about 55° C. Preferably, step (b) comprises cooling to temperature of: about 0° C. to about 30° C., about 10° C. to about 30° C., about 15° C. to about 28° C. or about 20° C. to about 25° C. Preferably, step (c) is carried out at a temperature of: about 20° C. to about 100° C., about 22° C. to about 90° C., or about 50° C. to about 80° C., preferably under reduced pressure or vacuum.

The crystalline Eluxadoline form alpha according to the present invention have a chemical purity of: about 99-100%, about 99.5%400% by HPLC, about 99.8 to 100%, or about 99.9-100% by HPLC, or may be substantially free of any other solid state form of Eluxadoline, preferably wherein the crystalline Eluxadoline form alpha contains less than 10%, less than 5% or less than 2% by weight of any other solid state form of Eluxadoline.

The present invention encompasses the use of the above-described crystalline Eluxadoline form alpha for preparing other solid state forms of Eluxadoline.

The present invention also comprises crystalline form alpha in stable form. The stable form alpha of the present invention can be characterized by an X-ray powder diffraction pattern as depicted in FIG. 5. The stable form alpha of the present invention can be further characterized by the SEM image as depicted in FIG. 6.

The stable form alpha of the present invention essentially does not convert to any other crystalline form of Eluxadoline, for example Eluxadoline hydrate, like form beta, in various conditions; i.e., contains not more than ("NMT") 10% (w/w) of any crystalline form. The content of crystalline form in the stable form alpha is typically measured by any suitable method appreciated by a skilled person in the art, for example PXRD, solid-state NMR, IR, Raman, or DSC. Using PXRD, for example, the content of crystalline Eluxadoline form Beta in stable form alpha will be measured by detecting and quantifying the described characteristic peaks of form beta (absent in form alpha). A skilled person in the art would typically identify and select the characteristic peaks of crystalline Eluxadoline form beta, for example according to the characteristic peaks described in U.S. Pat. Nos. 8,691,860 or 7,994,206. For example, the characteristic peaks of crystalline Eluxadoline form beta used for the above described measurement can be selected from the following list of peaks at about: 11.0, 12.4 and 15.2 degrees two theta ±0.2 degrees two theta. In specific embodiments, the stable form alpha contains not more than 10% (w/w) of any crystalline form when stored at 80% relative humidity ("RH") for 3 days, preferably for 8 days. In particular, the stable form alpha contains not more than 10% (w/w) of any crystalline form beta when stored at 80% relative humidity ("RH") for 3 days, preferably for 8 days. More preferably, the stable form alpha contains not more than 10% (w/w) of any crystalline form, particularly beta, when stored at the conditions specified in Table 3.

The present invention comprises a process for preparing stable form alpha, comprising:
i) dissolving amorphous Eluxadoline in methanol, preferably at a temperature of about from about 0° C. to about 25° C., preferably from about 0° C. to about 5° C., to obtain a clear solution;
ii) heating of the solution, preferably to a temperature of about from about 20° C. to about 65° C., preferably from 50-55° C. or from 50-65° C.; and
iii) cooling the obtained suspension, preferably to a temperature of about 0° C. to about 25° C., preferably to a temperature of about 0° C. to about 5° C. The process can further comprise filtering, washing, preferably with cold methanol, and drying the obtained solid, preferably under vacuum, at a temperature of about 60° C. for a period of about 16 h.

Preferably, Eluxadoline is dissolved in step i) at a ratio of from about 100 g/L to about 250 g/L, more preferably 100 g/L.

The heating in step ii) is done for a suitable time for example, from 2 hours to 16 hours, or preferably 4 hours. Typically, during this time form II of Eluxadoline is obtained.

The cooling in step iii) is done for a suitable time for example, from 1 hours to 4 hours, or 2 hours. In certain embodiments, the present invention comprises a suspension comprising form II and methanol. The process can further comprise filtering and washing, preferably with cold methanol. The obtained wet cake comprises form II pure or its mixture with form alpha. Wet cake is dried at about 60° C. for a period of about 16 h to get pure alpha with low residual solvent.

The present invention also comprises stable form alpha, as specified above, obtained by the above described process.

Figure 7:
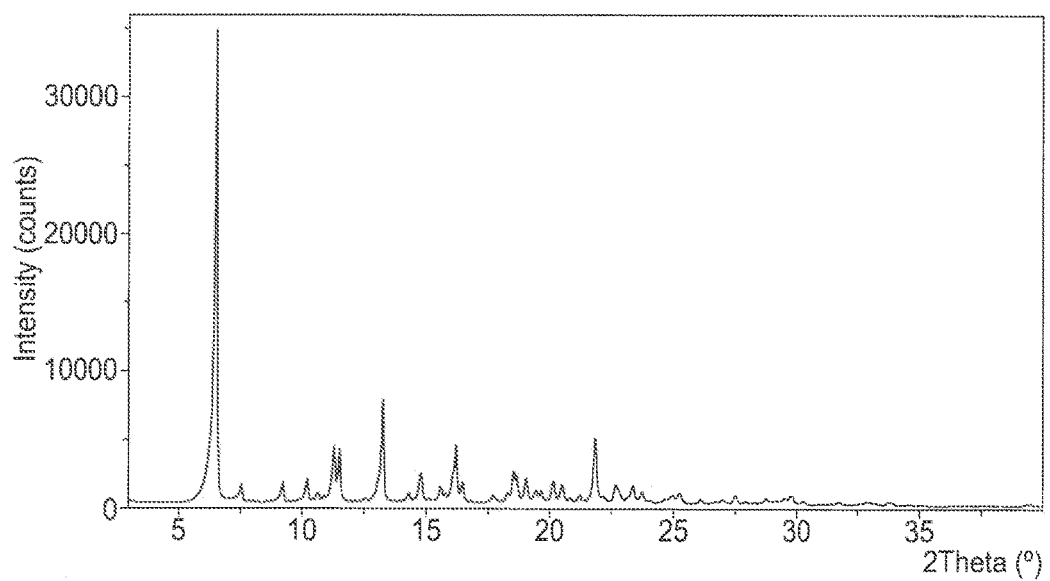
FIG. 7 shows an X-ray powder diffractogram of Eluxadoline form III.

In another embodiment, the present invention comprises crystalline Eluxadoline, designated form III, characterized by data selected from one or more of the following: X-ray powder diffraction pattern having peaks at about 9.3, 10.2, 11.5, 13.3 and 21.8 degrees two theta ±0.2 degrees two theta; an X-ray powder diffraction pattern as depicted in FIG. 7; and combinations of this data, wherein the crystalline form is an ethanol solvate or a mixture of hydrate and ethanol solvate.

Crystalline form III of Eluxadoline can be further characterized by the X-ray powder diffraction pattern having peaks at 9.3, 10.2, 11.5, 13.3 and 21.8 degrees two theta ±0.2 degrees two theta and also having any one, any two, any three or more additional peaks selected from 6.5, 11.2, 14.7, 16.1, 20.1±0.2 degrees two theta ±0.2 degrees two theta.

Crystalline form III of Eluxadoline may be characterized by each of the above characteristics alone and/or by all possible combinations.

Figure 8:
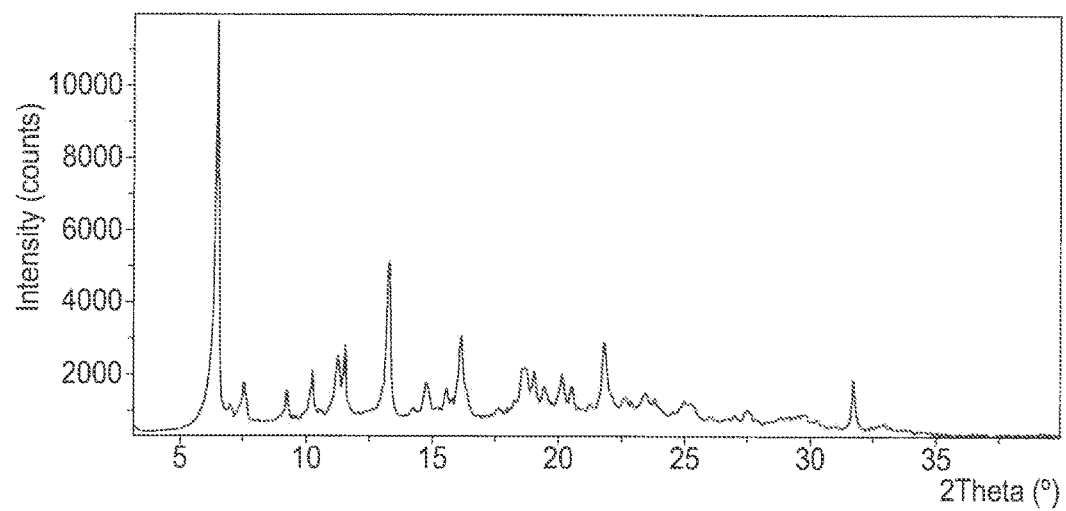
FIG. 8 shows an X-ray powder diffractogram of Eluxadoline form IV.
Figure 9:
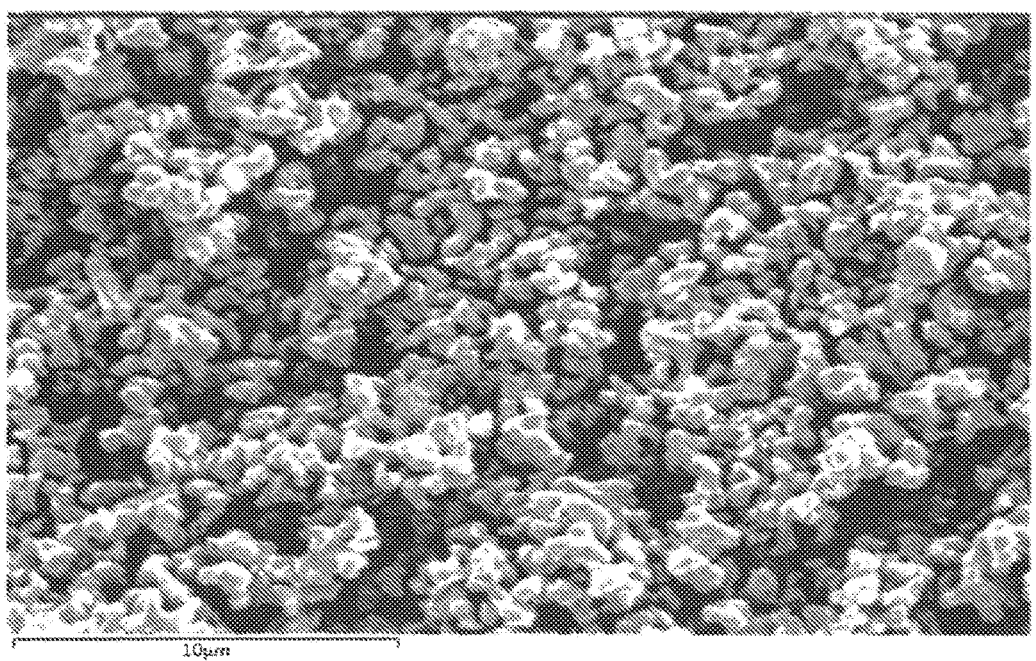
FIG. 9 shows an SEM image of stable amorphous Eluxadoline.

In yet another embodiment, the present invention comprises crystalline Eluxadoline, designated form IV, characterized by data selected from one or more of the following: X-ray powder diffraction pattern having peaks at about 9.3, 10.2, 11.5, 13.3 and 21.8 degrees two theta ±0.2 degrees two theta; an X-ray powder diffraction pattern as depicted in FIG. 8; and combinations of this data, wherein the crystalline form is an THF solvate or a mixture of hydrate and THF solvate.

Crystalline form IV of Eluxadoline can be further characterized by the X-ray powder diffraction pattern having peaks at 9.3, 10.2, 11.5, 13.3 and 21.8 degrees two theta ±0.2 degrees two theta and also having any one, any two, any three or more additional peaks selected from 6.5, 11.2, 14.7, 16.1, 20.1±0.2 degrees two theta ±0.2 degrees two theta.

Crystalline form IV of Eluxadoline may be characterized by each of the above characteristics alone and/or by all possible combinations.

The above described solid state forms of Eluxadoline can be used to prepare pharmaceutical compositions and formulations. In certain embodiments, the present invention comprises the above described solid state forms of Eluxadoline for use in the preparation of pharmaceutical compositions and formulations.

The present invention comprises pharmaceutical compositions and formulations comprising the solid state forms of Eluxadoline of the present invention. Typically, the pharmaceutical compositions and/or formulations are solid compositions and the Eluxadoline retains its solid state form.

The pharmaceutical formulations can be prepared by a process comprising combining the solid state forms of Eluxadoline of the present invention with at least one pharmaceutically acceptable excipient.

The above solid state forms of Eluxadoline of the present invention can also be used as a medicament, particularly for the treatment of gastrointestinal disorders.

The present invention further encompasses 1) the use of the above-described solid state forms of Eluxadoline in the manufacture of a pharmaceutical composition and/or formulations, and 2) a method of treating a subject suffering from irritable bowel syndrome with diarrhea (IBS-D) or otherwise in need of the treatment, comprising administration of an effective amount of a pharmaceutical composition comprising any one or a combination of the solid state forms of Eluxadoline described herein to a person in need of the treatment.

Having thus described the invention with reference to particular preferred embodiments and illustrative examples, those in the art can appreciate modifications to the invention as described and illustrated that do not depart from the spirit and scope of the invention as disclosed in the specification. The Examples are set forth to aid in understanding the invention but are not intended to, and should not be construed to limit its scope in any way.

X-Ray Powder Diffraction Method:

Sample after being powdered in a mortar and pestle is applied directly on a silicon plate holder. The X-ray powder diffraction pattern was measured with Philips X'Pert PRO X-ray powder diffractometer, equipped with Cu irradiation source=1.54184 Å(Ångström), X'Celerator (2.022° 2θ) detector. Scanning parameters: angle range: 3-40 deg., step size 0.0167, time per step 37 s, continuous scan.

SEM Method:

Samples were fixed on an aluminium stub with conductive double sided adhesive tape and coated with gold. Sputtered with gold by Edwards S150 sputter coater. Samples were scanned on Jeol JSM-5800 scanning microscope, EDS by the Oxford Aztec X-max 20 mm$^2$, Conditions: WD=20, HT=10 kV.

Particle Size Distribution Method:
PSD was determined on a Malvern Laser Diffraction Mastersizer 2000 using the following parameters:
  Measuring range: 0.02-2000 mcm
  Model: general purpose
  Sensitivity: normal
  Particle shape: irregular
  Particle name: Eluxadoline
  Refraction index of Eluxadoline: 1.64
  Absorption: 0.01
  Dispersant: n-hexane
  Refraction index of dispersant: 1.38
  Obscuration: 10-20%
  Pump/stirrer: 2500 rpm
  Sample measurement time: 5 sec
  Background measurement time: 10 sec
  Number of measurement cycles: 5
  External ultrasound: 15 sec
  Recirculation: 1.5 min
  Delay between measurements: 0 sec
  Number of sample preparations: 1
Preparation of Solutions
  Dilution medium: 0.2% w/v Dioctyl Sulfosuccinate Sodium Salt (DSSS), assay NLT 96%, in hexane.
    Dilution medium preparation: Transfer about 2 g Dioctyl Sulfosuccinate Sodium Salt (DSSS) into 1000 ml volumetric flask. Fill up to the mark with pure n-hexane and stir on magnetic stirrer until the DSSS dissolves.
Background Measurement
Blank Frequency
  A background measurement was performed before each measurement.
Background Measurement
  A measuring cell was slowly filled with n-hexane. The pump rate was increased to 2500 rpm. The dispersion unit was covered with the lid. Background was checked and background measurement was started. After alignment and background measurement, the % obscuration value should not exceed 0.1%. If the % obscuration value was greater than 0.1% the measuring cell was re-cleaned and the background measurement repeated to obtained a % obscuration of 0.1% or less.
Sample Measurement
Sample Preparation
  The sample was prepared as a concentrated suspension. The original sample was mixed in a bottle by easy rotating the bottle. Approximately 50 mg of sample was transferred to a 50 mL glass beaker. Several drops of 0.2% DSSS/n-hexane were added and the mixture was stirred very gently with the glass stick to make a uniform slurry; free from agglomerates and lumps. About 1 mL of 0.2% DSSS/n-hexane was added, and the mixture stirred gently with glass stick. About 40 mL of n-hexane was added, and the mixture was sonicated in an external ultrasound bath for 15 seconds. The dispersion was mixed afterwards by plastic pipette by suction.
  Start of Measurement
  After performing the background measurement, at the same stirrer and pump conditions (2500 rpm), the prepared sample suspension in a dispersion bath was added in small portions, until an obscuration of about 12.5%. Measurement was started when background was stable, after about 1.5 minute recirculation. The final % obscuration should be between 10-20%. If the residual is greater than 1.5%, the experiment was repeated.
  Report of Data
  Average data from 5 measurement repeat cycles.

EXAMPLES

Reference Example

Eluxadoline dihydrochloride can be prepared according to the procedure described in U.S. Pat. No. 7,741,356.

Example 1: Preparation of Amorphous Eluxadoline 13.6 g of Eluxadoline dihydrochloride was dissolved in water (140 ml) and the solution was added dropwise to a mixture of 2M NaOH (20 ml) and water (120 ml). When all solution was added, the pH of the mixture was adjusted to pH 6.6 and the mixture was stirred for 1 h at 0-5° C. The obtained suspension was filtered, and the obtained cake was washed with water and stirred at 50° C. for 10 h. 9.8 g of eluxadoline was obtained. the sample was characterized by PXRD—amorphous form was obtained (PXRD is shown in FIG. 1).

Example 2: Preparation of Eluxadoline Crystalline Form I

About 1 g of amorphous Eluxadoline was slurried in 10 ml tetrahydrofuran ("THF") at temperature of about 37° C. After 24 h wet sample from the obtained suspension was analysed by PXRD (form I was detected). The suspension was then filtered through filter paper placed in funnel and the obtained white solid was characterized by PXRD—Form I was obtained (FIG. 2).

Example 3: Preparation of Eluxadoline Crystalline Form Alpha

About 9.5 mg of form I was placed in DSC hermetic aluminium pan with a hole. The sample was heated on Q1000 MDSC (TA instruments) with heating rate of 10° C./min, under nitrogen flow of 50 ml/min. The sample was heated up to 140° C. and then kept isothermally for about 10 minutes. The pan was taken out of the DSC and cooled down to RT. The solid was taken out from the pan and was checked by PXRD.

Example 4: Preparation of Eluxadoline Crystalline Form II 1 gram of amorphous eluxadoline was placed in a closed bottle to be in contact with methanol vapor at 25° C. During this time, amorphous eluxadoline crystallizes in contact with methanol vapor until full conversion of amorphous to crystalline material is accomplished. The crystalline white powder was checked finally after 30 days and a new crystalline form of eluxadoline was found named form II.

Example 5: Preparation of Eluxadoline Crystalline Form II

Amorphous eluxadoline (0.75 g) was suspended in methanol (5 ml). Resulting suspension was heated at 50° C. over 4 h. Cooled reaction mixture (room temperature) was filtered off. White solid crystalline powder was checked by XRD and was found to be form II.

Example 6. Preparation of Eluxadoline Form Alpha

About 0.73 g of Eluxadoline Form II was dried for about 16 h at 60° C. and 10 mbar to obtain 0.35 g of Eluxadoline form alpha as was characterized by XRD.

Example 7: Preparation of Eluxadoline Form Alpha

Amorphous Eluxadoline (7 g) was suspended in tetrahydrofuran (42 ml). Resulting suspension was heated at 50° C. over 22.5 h. Cooled reaction mixture (room temperature) was filtered off and dried (23 h, 50° C., 10 mbar). Obtained solid Eluxadoline was characterized by XRD and confirmed to be form alpha (4 g).

Example 8: Preparation of Eluxadoline Form Alpha

Amorphous Eluxadoline (13.7 g) was suspended in tetrahydrofuran (68 ml). Resulting suspension was heated at reflux over 5.5 h. Cooled reaction mixture (room temperature) was filtered off. One portion of wet crystals was dried at 50° C. (16.5 h, 10 mbar). Second portion was dried at 100° C. (16.5 h, 10 mbar). In both cases Eluxadoline form alpha was obtained as was characterized by XRPD.

Example 9: Preparation of Eluxadoline Form Alpha

Amorphous Eluxadoline (16.5 g) was suspended in tetrahydrofuran (83 ml) and resulting suspension was heated at reflux over 3.5 h. Suspension was cooled to 0-5° C., stirred for 0.5 h, filtered off and solid was washed with cold THF. A portion of solid (7.6 g) was dried at 60° C. for 20 h yielding form alpha (5.99 g). Second portion (8.66 g) of solid was dried at 80° C. for 20 h yielding form alpha (6.6 g) as was characterized by XRPD.

Example 10: Preparation of Stable Amorphous Eluxadoline 17 g of eluxadoline hydrochloride was dissolved in water (175 ml) while warming. The solution, cooled to room temperature, was added dropwise to a mixture of water (120 ml) and 2M NaOH (30 ml) and the pH was adjusted to 6.6 upon addition. Suspension was stirred at RT for 1 h and additionally at 0-5° C. for 1 h and suctioned off. Cake was washed with cold water and dried at 50° C. for 15 h yielding 13.5 g of amorphous eluxadoline.

The obtained amorphous form was stored at various conditions, and the PXRD was analyzed after 3 and 7 days:

TABLE 1

| % RH | PXRD results - after 7 days | % weight loss/water cont. - after 7 days |
|---|---|---|
| As is | amorphous | TGA-5.97% |
| 0% | amorphous | TGA-7.96% |
| 20% | amorphous | TGA-7.96%/KF-9.01% |
| 40% | amorphous | TGA-8.15%/KF-9.11% |
| 60% | amorphous | TGA-8.88%/KF-9.91% |
| 80% | amorphous | TGA-11.88%/KF-13.30% |
| 100% | amorphous | TGA-15.03/KF-15.69% |

The above results indicate that all samples exposed to RH 0-10% for a 7 day period, did not show any changes, and hence amorphous Eluxadoline is surprisingly very stable.

Example 11: Preparation of Stable Amorphous Eluxadoline

Methyl 5-(((S)-2-amino-3-(4-carbamoyl-2,6-dimethylphenyl)-N—((R)-1-(4-phenyl-1H-imidazol-2-yl)ethyl)propanamido)methyl)-2-methoxybenzoate was suspended in mixture of THF (200 ml) and water (749 ml) and into a cooled mixture to 10-15° C. 6M NaOH (51 ml) was added dropwise at the same temperature. Mixture was warmed to room temperature, stirred for 4 h and water (600 ml) was added. pH of the mixture was adjusted to 9.5 with HCl and THF was distilled off. pH of the mixture was adjusted to 6.9 and the mixture was stirred at room temperature overnight and 2.5 h at 0-5° C. The mixture was suctioned off and cake was washed with water (2×160 ml) and dried at 45° C. for 18 h yielding 28.4 g of amorphous eluxadoline; HPLC: 99.22 A %.

The obtained pure amorphous form was stored at various conditions, and the PXRD was analyzed after 3 and 7 days:

TABLE 2

| RH | PXRD results after 7 days |
|---|---|
| 0% | amorphous |
| 20% | amorphous |
| 40% | amorphous |
| 60% | amorphous |
| 80% | amorphous |
| 100% | amorphous |

Example 12: Preparation of Stable Form Alpha of Eluxadoline

Amorphous 5-(((S)-2-amino-3-(4-carbamoyl-2,6-dimethylphenyl)-N—((S)-1-(4-phenyl-1H-imidazol-2-yl)ethyl)propanamido)methyl)-2-methoxybenzoic acid (3 g) was dissolved in methanol (15 ml). Solution was heated to 50° C. and stirred for 4 h. Resulting suspension was cooled to temperature of from 0 to 5° C., diluted with methanol (2 mL) and stirred for 30 min. Solid was filtered and washed with methanol. White solid was dried for 16 h at 60° C. and 10 mbar to obtain 2.31 g of 5-(((S)-2-amino-3-(4-carbamoyl-2,6-dimethylphenyl)-N—((S)-1-(4-phenyl-1H-imidazol-2-yl)ethyl)propanamido)methyl)-2-methoxybenzoic acid, form alpha as was characterized by XRD, PXRD pattern is shown in FIG. 5; SEM image is shown in FIG. 6.

The obtained form alpha was stored at various conditions, and the PXRD was analyzed after 3 and 8 days:

TABLE 3

| RH | PXRD results after 8 days |
|---|---|
| as is | alpha (% weight loss after 8 days by TGA* = 1.29%) |
| 0% | alpha |
| 20% | alpha |
| 40% | alpha |
| 60% | alpha |
| 80% | alpha |

*TGA up to 121° C.

Example 13: Preparation of Form III of Eluxadoline

Amorphous 5-(((S)-2-amino-3-(4-carbamoyl-2,6-dimethylphenyl)-N—((S)-1-(4-phenyl-1H-imidazol-2-yl)ethyl)propanamido)methyl)-2-methoxybenzoic acid (3 g) was suspended in absolute ethanol (15 ml). The obtained suspension was heated to 50° C., stirred for 16 h and then cooled to a temperature of about temperature of from 0° C. to 5° C. and stirred for 30 minutes. The obtained solid was filtered and washed with absolute ethanol, and a white solid crystalline powder (3.4 g) was obtained. The product was analyzed by XRD, form III was obtained—PXRD pattern is shown in FIG. 7

Example 14: Preparation of Form IV of Eluxadoline

Amorphous Eluxadoline (1 g) was suspended in THF (3 ml) and warmed up to reflux temperature, then additional amount of THF was added (2 ml). The mixture was stirred overnight at the reflux temperature and solvent evaporated and fresh amount of THF was added and suspension was obtained. Additional amount of THF was added (3 ml), and the obtained suspension was filtered, dried at 50° C. for 22 hr; the dried product was analyzed by XRD, form IV was obtained—PXRD pattern is shown in FIG. 8.

Example 15: Preparation of Form Alpha of Eluxadoline

Amorphous 5-(((S)-2-amino-3-(4-carbamoyl-2,6-dimethylphenyl)-N—((S)-1-(4-phenyl-1H-imidazol-2-yl)ethyl)propanamido)methyl)-2-methoxybenzoic acid (3 g) was dissolved in methanol (15 ml). The obtained solution was filtered and heated to 50° C.-55° C. and stirred for 4 hours. The resulting suspension was cooled to a temperature of from about 0° C. to about 5° C. and stirred for 2 hours. The obtained solid was filtered and washed with methanol. The obtained white solid crystalline powder was dried for 16 hours at 60° C. and 10 mbar to obtain 2.8 g of 5-(((S)-2-amino-3-(4-carbamoyl-2,6-dimethylphenyl)-N—((S)-1-(4-phenyl-1H-imidazol-2-yl)ethyl)propanamido)methyl)-2-methoxybenzoic acid. The product was analyzed by PXRD, form alpha was obtained.

Example 16: Preparation of Form Alpha of Eluxadoline

Amorphous 5-(((S)-2-amino-3-(4-carbamoyl-2,6-dimethylphenyl)-N—((S)-1-(4-phenyl-1H-imidazol-2-yl)ethyl)propanamido)methyl)-2-methoxybenzoic acid (3 g) was dissolved in methanol (15 ml). The obtained solution was filtered and stirred for 5 hours at room temperature. The resulting suspension was cooled to a temperature of from about 0° C. to about 5° C. and stirred for 2 hours. The obtained solid was filtered and washed with methanol. The resulting white solid crystalline powder was dried for 16 hours at 60° C. and 10 mbar to obtain 2.7 g of 5-(((S)-2-amino-3-(4-carbamoyl-2,6-dimethylphenyl)-N—((S)-1-(4-phenyl-1H-imidazol-2-yl)ethyl)propanamido)methyl)-2-methoxybenzoic acid. The product was analyzed by PXRD, form alpha was obtained.

Example 17: Preparation of Form Alpha of Eluxadoline

Amorphous 5-(((S)-2-amino-3-(4-carbamoyl-2,6-dimethylphenyl)-N—((S)-1-(4-phenyl-1H-imidazol-2-yl)ethyl)propanamido)methyl)-2-methoxybenzoic acid (20 g) was dissolved in methanol (150 ml). The obtained solution was filtered and additional methanol (50 mL) was added. The solution was heated to 50° C.-55° C. and stirred for 4 hours. The resulting suspension was cooled to a temperature of from about 0° C. to about 5° C. and stirred for 2 hours. The obtained solid was filtered and washed with methanol. The resulting white solid crystalline powder was dried for 16 h at 60° C. and 10 mbar to obtain 16.7 g of 5-(((S)-2-amino-3-(4-carbamoyl-2,6-dimethylphenyl)-N—((S)-1-(4-phenyl-1H-imidazol-2-yl)ethyl)propanamido)methyl)-2-methoxybenzoic acid. The product was analyzed by PXRD, form alpha was obtained.

Example 18: Preparation of Form Alpha of Eluxadoline

Amorphous 5-(((S)-2-amino-3-(4-carbamoyl-2,6-dimethylphenyl)-N—((S)-1-(4-phenyl-1H-imidazol-2-yl)ethyl)propanamido)methyl)-2-methoxybenzoic acid (50 g) was dissolved in methanol (375 ml). The obtained solution was filtered and additional methanol (125 mL) was added. The solution was heated to 50° C.-55° C. and stirred for 4 hours. The resulting suspension was cooled to a temperature of from about 0° C. to about 5° C. and stirred for 2 hours. The obtained solid was filtered and washed with methanol. The resulting white solid crystalline powder was dried for 16 hours at 60° C. and 10 mbar to obtain 5-(((S)-2-amino-3-(4-carbamoyl-2,6-dimethylphenyl)-N—((S)-1-(4-phenyl-1H-imidazol-2-yl)ethyl)propanamido)methyl)-2-methoxybenzoic acid. The product was analyzed by PXRD, form alpha was obtained.

Example 19: Preparation of Eluxadoline Form Alpha

Amorphous 5-(((S)-2-amino-3-(4-carbamoyl-2,6-dimethylphenyl)-N—((S)-1-(4-phenyl-1H-imidazol-2-yl)ethyl)propanamido)methyl)-2-methoxybenzoic acid (55 g) was dissolved in methanol (400 mL). Solution was filtered and additional methanol (150 mL) was added. Solution was heated to 50° C. and stirred for 4 h. Resulting suspension was cooled to 0-5° C. and stirred for 2 h. Solid was filtered and washed with methanol. White solid crystalline powder was dried for 16 h at 60° C. and 10 mbar to obtain 44.09 g of 5-(((S)-2-amino-3-(4-carbamoyl-2,6-dimethylphenyl)-N—((S)-1-(4-phenyl-1H-imidazol-2-yl)ethyl)propanamido)methyl)-2-methoxybenzoic acid, form alpha as was characterized by XRD; HPLC: 99.82 A %.

Figure 14A:
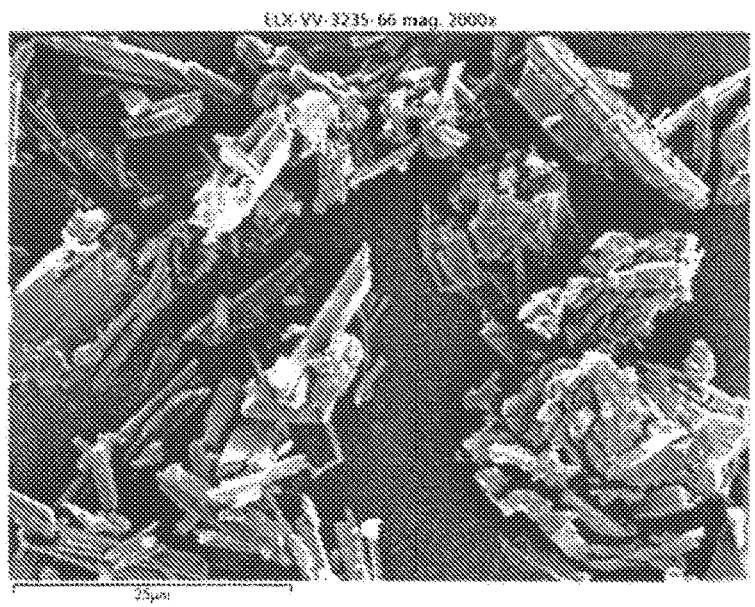
FIG. 14A and FIG. 14B: SEM images of stable Eluxadoline form alpha of Example 19 at 2000× magnification and at 5000× magnification respectively.
Figure 14B:
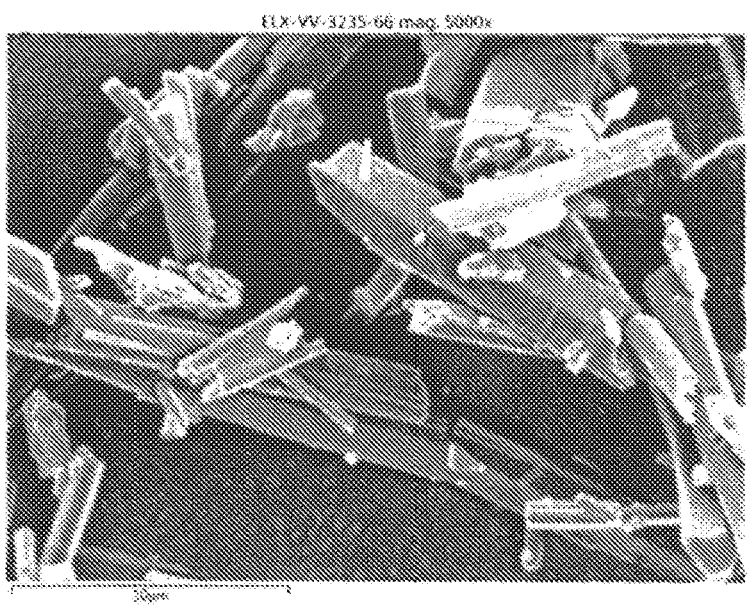
Figure 15:
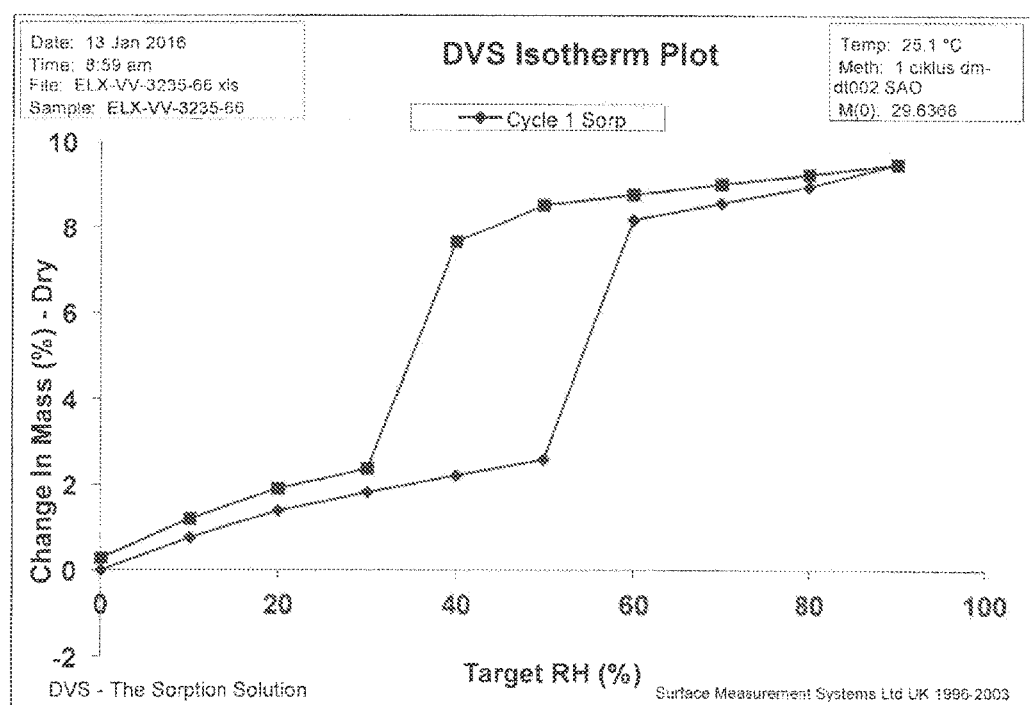
FIG. 15: DVS isotherm of stable Eluxadoline form alpha prepared according to Example 19.
Figure 19:
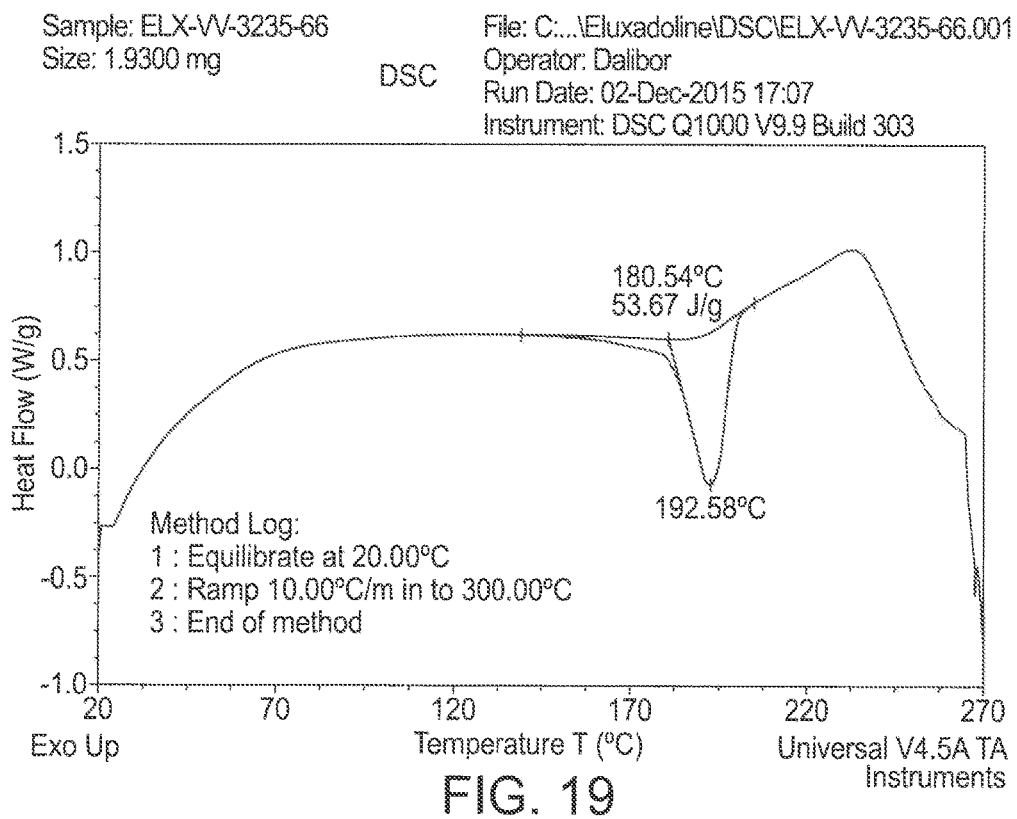
FIG. 19: DSC Thermogram of Eluxadoline Form alpha from Example 19.

XRPD pattern is shown in FIG. 13; SEM image is shown in FIGS. 14A and 14B; DVS image is shown in FIG. 15; DSC thermogram is show in FIG. 19: and TGA thermogram is shown in FIG. 20.

Example 20. Preparation of Pure and Stable Amorphous Eluxadoline

Methyl 5-(((S)-2-amino-3-(4-carbamoyl-2,6-dimethylphenyl)-N—((S)-1-(4-phenyl-1H-imidazol-2-yl)ethyl)propanamido)methyl)-2-methoxybenzoate dihydrochloride (10.0 kg, 15.23 mol), water (187 L) and tetrahydrofuran (50 L) was added into 250 L reactor. The pH of the mixture was set to 13 with sodium hydroxide solution (6M) and additional quantity of sodium hydroxide solution was added (6.35 L, 38.1 mol). The reaction mixture was stirred for 6 hours at 20-25° C., upon which the pH of the reaction mixture was set to 9-10 and the THF was distilled off by vacuum evaporation. The water solution of obtained Eluxadoline was washed twice with ethylacetate (133 L) and residue of the ethylacetate was removed from water layer by vacuum evaporation. pH of the solution was adjusted to 6-7 with hydrochloric solution (2M) and obtained suspension was heated till 40° C., stirred for 2 hours and cooled till 0-5° C. Suspension was stirred for 2 hours at 0-5° C. Obtained crystals were centrifuged, washed with water (2×20 L) and dried under vacuum. 7.6 kg (82% yield, assay 93.77%) of 5-(((S)-3-amino-4-(4-carbamoyl-2,6-dimethylphenyl)-N—((S)-1-(4-phenyl-1H-imidazol-2-yl)ethyl)butanamido)methyl-2-methoxybenzoic acid was obtained, with HPLC purity of 99.94% area.

The obtained amorphous form was stored at various conditions of relative humidity, and the PXRD was obtained after 1M (Table 4):

TABLE 4

Polymorph stability properties of Eluxadoline amorphous (Example 20):

| % RH | PXRD results - after 1 M | % weight loss/water cont. - after 1 M |
|---|---|---|
| As is | amorphous | TGA-5.79% |
| 0% | amorphous | TGA-7.42% |
| 20% | amorphous | TGA-8.42% |
| 40% | amorphous | TGA-9.34% |
| 60% | amorphous | TGA-10.36% |
| 80% | amorphous | TGA-12.89% |
| 100% | amorphous | TGA-15.23% |

*TGA up to 190° C.
**HPLC result does not show any changes in comparison to start, sample 1 M/0-100% RF

Example 21. Preparation of Pure and Stable Amorphous Eluxadoline

Methyl 5-(((S)-2-amino-3-(4-carbamoyl-2,6-dimethylphenyl)-N—((S)-1-(4-phenyl-1H-imidazol-2-yl)ethyl)propanamido)methyl)-2-methoxybenzoate dihydrochloride (7.25 kg, 11.04 kmol), water (13.9 L) and tetrahydrofuran (36 L) was added into 250 L reactor. The pH of the mixture was set to 13 with sodium hydroxide solution (6M) and additional quantity of sodium hydroxide solution was added (4.6 L, 38.1 mol). The reaction mixture was stirred for 6 hours at 20-25° C., upon which the pH of the reaction mixture was set to 9-10 and the THF was distilled off by vacuum evaporation. The water solution of obtained Eluxadoline was washed twice with ethylacetate (2×97 L) and residue of the ethylacetate was removed from water layer by vacuum evaporation. pH of the solution was adjusted to 6-7 with hydrochloric solution (2M) and obtained suspension was heated till 40° C., stirred for 2 hours and cooled till 0-5° C. Suspension was stirred for 2 hours at 0-5° C. Obtained crystals were centrifuged, washed with water (2×20 L) in the fluidized bed dryer at 45° C. till LOD 8%. The material was additionally dried in the vacuum tray drier till LOD 2.23%. 5.06 kg (75.7% yield, assay 94.10%) of 5-(((S)-3-amino-4-(4-carbamoyl-2,6-dimethylphenyl)-N—((S)-1-(4-phenyl-1H-imidazol-2-yl)ethyl)butanamido)methyl-2-methoxybenzoic acid was obtained, with HPLC purity of 99.64% area.

DVS image is shown in FIG. 11. The obtained amorphous form was stored at various conditions, and the PXRD was obtained after 2M (Table 5):

TABLE 5

Polymorph stability properties of Eluxadoline amorphous (Example 21):

| % RH | PXRD results - after 2 M | % weight loss/water cont. after 2 M KF |
|---|---|---|
| As is | amorphous | 4.42% |
| 0% | amorphous | 8.56% |
| 20% | amorphous | 9.17% |
| 40% | amorphous | 10.50% |

TABLE 5-continued

Polymorph stability properties of Eluxadoline amorphous (Example 21):

| % RH | PXRD results - after 2 M | % weight loss/water cont. after 2 M KF |
|---|---|---|
| 60% | amorphous | 11.93% |
| 80% | amorphous | 14.15% |
| 100% | amorphous | 14.54% |

*TGA up to 190° C.
**HPLC result does not show any changes in comparison to start, sample 2 M/0-100% RH Specific surface area measurement using the procedure described in Example 29, for amorphous form: 1.243 m²/g.

Example 22. Preparation of Form Alpha of Eluxadoline

Methanol (18 L) was charged in the 50 L reactor and cooled to 0-5° C. followed by the portionwise addition of 5-(((S)-3-amino-4-(4-carbamoyl-2,6-dimethylphenyl)-N—((S)-1-(4-phenyl-1H-imidazol-2-yl)ethyl)butanamido)methyl-2-methoxybenzoic acid precipitated from water at pH 6.5 (2.29 kg assay 92.49%, 3.72 mol). The suspension was stirred till dissolving, and filtrated through the filter lense at 0-5° C. and washed with methanol (2.1 L) cooled to 0-5° C. The mixture is heated to 60° C., stirred for 4 hours. The suspension was cooled to 0-5° C. and stirred for additional period of 140 minutes. The crystals were filtered in the filter dryer, washed with methanol (2×2.3 L) and dried under vacuum at maximal temperature of 60° C. till LOD <1% with stirring applied after LOD <one (1)% for five (5) hours. White crystals were identified as 5-(((S)-3-amino-4-(4-carbamoyl-2,6-dimethylphenyl)-N—((S)-1-(4-phenyl-1H-imidazol-2-yl)ethyl)butanamido)methyl-2-methoxybenzoic acid, form alpha. The product was isolated in 84.4% yield (1.79 kg) with HPLC purity of 99.87% area.

Figure 21:
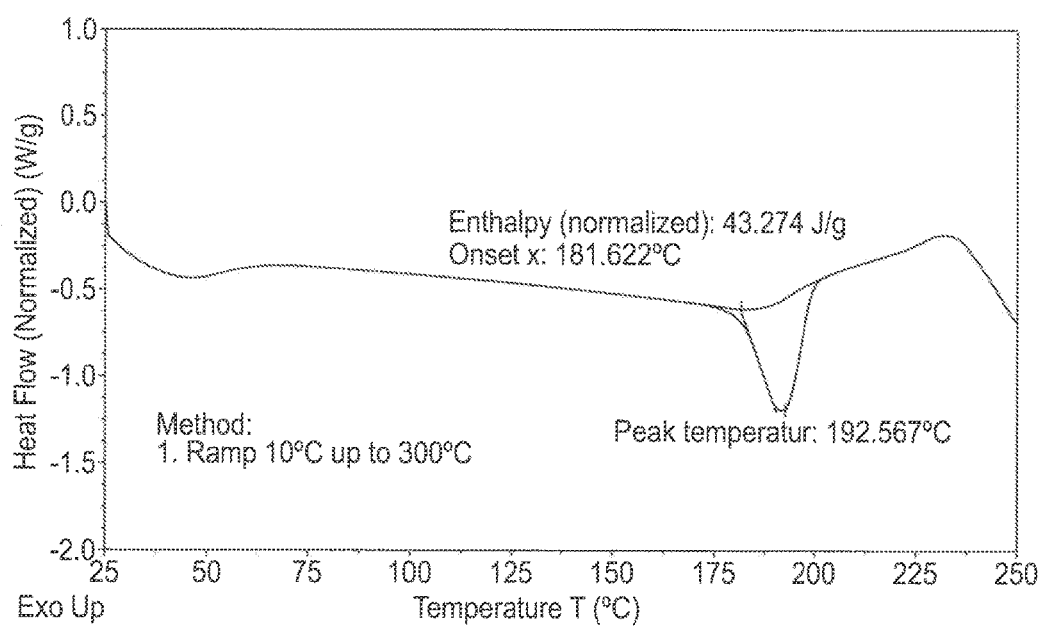
FIG. 21: DSC Thermogram of Eluxadoline Form alpha from Example 22.

XRPD pattern is shown in FIG. 16; SEM image is shown in FIG. 17; DSC thermogram is shown in FIG. 21 and TGA thermogram is shown in FIG. 22. The obtained form alpha was stored at various conditions, and the PXRD was obtained after 8, 14, and 21 days (Table 6):

TABLE 6

Polymorph stability properties of Eluxadoline alpha form (Example 22).

| % RH | PXRD results - after 21 days | % weight loss/water cont. - after 21 days |
|---|---|---|
| As is | alpha | TGA-0.95%/KF-1.12% |
| 0% | alpha | TGA-0.96 |
| 20% | alpha | TGA-1.26 |
| 40% | alpha | TGA-1.46 |
| 60% | alpha | TGA-6.30 |
| 80% | alpha | TGA-7.00 |
| 100% | alpha | TGA-9.01 |

*TGA up to 121° C.

Example 23. Thermal Stability at Different Relative Humidity

Samples of Eluxadoline alpha (5 g) were subjected to heating in a vacuum dryer at 50° C. and 100° C., for different periods of time. XRPD, and HPLC results show that Eluxadoline form alpha is stable (Table 7).

TABLE 7

Polymorph stability properties of Eluxadoline alpha form

| Temperature/ °C. | Time/h | XRPD | HPLC/Area % (start: 99.88) |
|---|---|---|---|
| 50 | 1 | alpha | — |
| 50 | 2 | alpha | — |
| 50 | 3 | alpha | 99.91 |
| 100 | 1 | alpha | — |
| 100 | 2 | alpha | — |
| 100 | 3 | alpha | 99.91 |

Example 24. Solubility

Solubility of Eluxadoline Form Alpha and Amorphous Samples
Solubility at Aqueous Buffer pH=2

The solubility was determined by placing 230 mg Eluxadoline samples into 15 ml TPP centrifuge tubes (Sigma) and 3 ml of solvent were added. Tubes were stoppered and shaken at 150 cpm for 24 hours at 37±0.2° C. in an incubator shaker (Innova 4080, New Brunswick Scientific). Suspensions were then filtered through 0.45 μm PTFE syringe filter and Eluxadoline concentrations were determined by HPLC.

Solubility at Aqueous Buffer pH=4

The solubility was determined by placing 130 mg of Eluxadoline samples into 15 ml TPP centrifuge tubes (Sigma) and 9 ml of solvent was added. Tubes were stoppered and shaken at 150 cpm for 24 hours at 37±0.2° C. in incubator shaker (Innova 4080, New Brunswick Scientific). Suspensions were then filtered through 0.45 μm PTFE syringe filter and Eluxadoline concentrations were determined by HPLC.

Solubility at Aqueous Buffer pH=6.8

The solubility was determined by placing 300 mg Eluxadoline samples into 15 ml TPP centrifuge tubes (Sigma) and 9 ml of solvent was added. Tubes were stoppered and shaken at 150 cpm for 24 hours at 37±0.2° C. in incubator shaker (Innova 4080, New Brunswick Scientific). Suspensions were then filtered through 0.45 μm PTFE syringe filter and Eluxadoline concentrations were determined by HPLC.

Example 25. Dissolution

Dissolution of Eluxadoline Form Alpha and Amorphous Sample

Samples were prepared and analysed in duplicate. About 20 mg of each sample were weighed into 500 ml Erlenmeyer flask, 200 ml of 50 mM phosphate buffer pH=7.4, previously heated to 37° C. were added and flasks were shaken at 110 rpm for 60 minutes at 37±0.2° C. in an incubator shaker. 3 ml aliquots were taken at 5, 10, 20, 30, 45 and 60 min, filtered through 0.45 μm Chromafil Xtra RC 45/25 syringe filter and analysed by UV/VIS spectrometer (absorbance at 203 nm).

The measurement was performed using the following instruments:
pH/Ion meter PHM 240, MeterLab, Radiometer Analytical
Incubator shaker Innova 4080, New Brunswick Scientific, 19 mm diameter circular orbit
UV/VIS spectrometer Varian Cary 50 Bio, 1 mm quartz cell Results of Eluxadoline samples dissolution in 50 mM phosphate buffer pH=7.4 are summarized in Table 8 below:

TABLE 8

Eluxadoline form alpha samples (example 22), and amorphous form (example 20) dissolution in 50 mM phosphate buffer pH = 7.4 at 37° C.

| time/min | ELX S-3-FIV (example 22) /% dissolved | ELX S2-FIII (example 20) /% dissolved |
|---|---|---|
| 5 | 83.62 | 63.21 |
| 10 | 91.02 | 81.56 |
| 20 | 95.48 | 91.46 |
| 30 | 95.87 | 93.81 |
| 45 | 96.56 | 94.48 |
| 60 | 96.64 | 94.50 |

Example 26. Bulk Density/Tapped Density (Hausner Ratio and Carr Index)

Bulk density/tapped density and corresponding Hausner ratio and Carr index were determined according to Ph. Eur. 2.9.34. Method 1.

Flowability properties of Eluxadoline form alpha (example 22) are given in table below (Table 9).

TABLE 9

Flowability properties of Eluxadoline form alpha

| Eluxadoline alpha | PSD/ μm | Bulk density (mg/mm$^3$) | Tapped density (mg/mm$^3$) | Hausner ratio | Flow character | Carr's index (%) | Flow character |
|---|---|---|---|---|---|---|---|
| Example 22 | 3/8/24 | 0.33 | 0.39 | 1.18 | Free flowing | 14.93 | good |

The low value of Carr index and Hausner ratio is indicative of a good flowability and compressibility of the form alpha of the present invention.

Example 27. Flow Function Determination

The Flow function was determined by using FT4 Powder Rheometer, Freeman FT4 instrument, and standard Freeman shear test—9 kPa (using small cell 1 ml), according to method below:

Method:
1. Compact to 9 kPa for 60 s
2. Pre shear hold 7 kPa for 16 s
3. Shear test at 7 kPa (Shear at 18°/min for 10°, auto detected peak torque yes)
4. Pre shear hold 6 kPa for 16 s
5. Shear test at 6 kPa (Shear at 18°/min for 10°, auto detected peak torque yes)
6. Pre shear hold 5 kPa for 16 s
7. Shear test at 5 kPa (Shear at 18°/min for 10°, auto detected peak torque yes)

8. Pre shear hold 4 kPa for 16 s
9. Shear test at 4 kPa (Shear at 18°/min for 10°, auto detected peak torque yes)
10. Pre shear hold 3 kPa for 16 s
11. Shear test at 3 kPa (Shear at 18°/min for 10°, auto detected peak torque yes)

Flow function of Eluxadoline form alpha (example 22) are given in table below (Table 10):

TABLE 10

Flow function of Eluxadoline amorphous form

| Sample | PSD/μm | Flow Function, (FF) | Classification of powder flowability after Jenike |
|---|---|---|---|
| Eluxadoline amorphous-Example 21 | 10/60/164 | 10.08 | Free-flowing |

Example 28. Texture Analysis/Density at 0.2 MPa

A simple and low sample consuming method for evaluation of the packing density of powders were obtained as compression profiles under low pressures using a die and a flat-faced punch fitted on a TA-XTplus Texture analyser (Stable Micro Systems Ltd., Godalming, UK). The small amount of 200 mg of sample is compressed in a steel mould (with the rate of displacement 0.03 mm/s). Also, a cyclic procedure (similar to tapping) was performed at maximal compressive displacement 0.5 mm, then retracting, relaxation for 15 s and then repeated compressive steps (altogether up to 20 steps).

Density at 0.2 MPa of Eluxadoline form alpha (example 22) depending on PSD are given in table below (Table 11).

TABLE 11

Density at 0.2 MPa of Eluxadoline form alpha vs. PSD value

| Eluxadoline alpha | PSD/μm | Density at 0.2 MPa/mg/mm$^3$ |
|---|---|---|
| Example 22 | 3/8/24 | 0.4707 |
| Eluxadoline alpha-lower particle size | 2/6/21 | 0.5190 |

The above results show that Eluxadoline form alpha has good compressibility properties. These results, as well as morphology properties correlate well with the SSA value of about 9.63 m$^2$/g below.

Example 29. Specific Surface Area (SSA) Measurement (Bet Nitrogen)

Apparatus

Specific Surface Area (SSA) measurements (Bet Nitrogen) were determined using a Micromeritics ASAP 2000, specific surface area analyzer. Samples were subjected to the BET nitrogen adsorption analysis to determine the specific surface of the samples.

Setup
Adsorbate: Nitrogen
Sample tube: 10 cc bulb with ½" stem
Sample mass: Approximately ½ full cell
Sample preparation: Degassing with nitrogen
Outgassing conditions: 40° C. (30 min)
Isothermal jacket: Used
Isothermal collection point: 20 adsorption points, in the range 0-1 P/P$_0$
Isothermal data analysis range: 5 point BET in the range 0.05-0.20 P/P$_0$
Leak test: 120 s
Free space: Measured
Evacuation time: 1 h
Outtest duration: 180 s
Equilibration interval: 5 s
Equilibration time out: 600 s SSA of Eluxadoline form alpha (example 22) are given in table below (Table 12).

TABLE 12

SSA of Eluxadoline form alpha

| Eluxadoline alpha | PSD/μm | SSA/m$^2$/g. |
|---|---|---|
| Example 22 | 3/8/24 | 9.63 |

The invention claimed is:

1. Stable amorphous Eluxadoline, which contains not more than 10% (w/w) of any crystalline form, or no detectable amount of any crystalline form, when stored at 25° C. and at:
    0% relative humidity for 3 days, and for 7 days, or
    20% relative humidity for 3 days, and for 7 days, or
    40% relative humidity for 3 days, and for 7 days, or
    60% relative humidity for 3 days, and for 7 days, or
    80% relative humidity for 3 days, and for 7 days, or
    100% relative humidity for 3 days, and for 7 days.

2. Stable amorphous Eluxadoline according to claim 1, which does not convert to crystalline Eluxadoline under conditions of 0-100% relative humidity at 25° C. for 7 days.

3. Stable amorphous Eluxadoline according to claim 1, which contains not more than 5%, or no detectable amount, of any crystalline form, when exposed to 0-100% relative humidity at 25° C. for 30 days.

4. Stable amorphous Eluxadoline according to claim 1, which contains not more than 5%, or no detectable amount, of any crystalline form, when exposed to 0-100% relative humidity at 25° C. for 60 days.

5. Stable amorphous Eluxadoline according to claim 1, characterized by an XRD pattern having a typical amorphous halo, or having an XRD pattern as depicted in FIG. 1.

6. Stable amorphous Eluxadoline according to claim 1, which contains not more than 10% (w/w) of any crystalline form of Eluxadoline, or not more than 10% (w/w) of form beta or form alpha.

7. Stable amorphous Eluxadoline according to claim 6, wherein form alpha is characterized by XRPD peaks selected from: 10.2, 11.3, 11.8, 14.0, 14.3 and 14.7 degrees two theta ±0.2 degrees two theta, and form beta is characterized by XRPD peaks selected from: 11.0, 12.4 and 15.2 degrees two theta ±0.2 degrees two theta.

8. Stable amorphous Eluxadoline according to claim 1 having a particle size distribution d(0.9) of from 100-250 μm.

9. Stable amorphous Eluxadoline according to claim 1, having a particle size distribution of: d (0.1)=1-4 μm, d(0.5)=15-25 μm and d(0.9)=100-250 μm.

10. Stable amorphous Eluxadoline according to claim 1, having a dissolution of greater than about 85%, greater than about 90%, or greater than about 94%, after 60 minutes at 37° C. in 50 mM phosphate buffer at pH 6.8.

11. Stable amorphous Eluxadoline according to claim 1, having a solubility of about 3 to about 10 mg/ml, about 3 to about 8 mg/ml, or about 4 to about 6 mg/ml at 37° C. in 50 mM phosphate buffer at pH 2 and/or pH 6.8, and a solubility of about 6 to about 15 mg/ml, about 7 to about 12 mg/ml, or about 8 to about 10 mg/ml at 37° C. in 50 mM phosphate buffer at pH 4.

12. Stable amorphous Eluxadoline according to claim 1, having a particle morphology according to FIG. 10.

13. Stable amorphous Eluxadoline according to claim 1, having a chemical purity of: about 99-100%, about 99.5%-100% by HPLC, about 99.8 to 100%, or about 99.9-100% by HPLC.

14. Stable amorphous Eluxadoline according to claim 1, which is substantially free of any crystalline form of Eluxadoline, or wherein the amorphous Eluxadoline contains less than 10%, less than 5% or less than 2% by weight of any crystalline form of Eluxadoline.

15. A pharmaceutical composition or dosage form comprising stable amorphous Eluxadoline according to claim 1, and at least one pharmaceutically acceptable excipient, wherein the stable amorphous Eluxadoline retains its solid state form in the pharmaceutical composition or dosage form.

16. A process for preparing a pharmaceutical composition or dosage form comprising combining stable amorphous Eluxadoline according to claim 1, with at least one pharmaceutically acceptable excipient, wherein the stable amorphous Eluxadoline retains its solid state form in the pharmaceutical composition or dosage form.

17. A method of treating a subject suffering from irritable bowel syndrome with diarrhea (IBS-D) or otherwise in need of the treatment, comprising administering to the subject an effective amount of a pharmaceutical composition comprising stable amorphous Eluxadoline of claim 15.

\* \* \* \* \*